US010149697B2

(12) United States Patent
Avneri et al.

(10) Patent No.: US 10,149,697 B2
(45) Date of Patent: Dec. 11, 2018

(54) DEVICES AND METHODS FOR PERCUTANEOUS TISSUE REMOVAL

(71) Applicant: Angioworks Medical B.V., Amsterdam (NL)

(72) Inventors: Ben-Ami Avneri, Moshav Udim (IL); Shahar Avneri, Herzliya (IL); Itzhak Avneri, Tel Aviv-Jaffa (IL)

(73) Assignee: ANGIOWORKS MEDICAL, B.V., Amsterdam (NL)

( * ) Notice: Subject to any disclaimer, the term of this patent is extended or adjusted under 35 U.S.C. 154(b) by 142 days.

(21) Appl. No.: 14/349,920

(22) PCT Filed: Oct. 4, 2012

(86) PCT No.: PCT/IB2012/002847
§ 371 (c)(1),
(2) Date: Apr. 4, 2014

(87) PCT Pub. No.: WO2013/050880
PCT Pub. Date: Apr. 11, 2013

(65) Prior Publication Data
US 2014/0296889 A1    Oct. 2, 2014

Related U.S. Application Data

(60) Provisional application No. 61/542,901, filed on Oct. 4, 2011.

(51) Int. Cl.
*A61B 17/22*      (2006.01)
*A61B 17/3207*    (2006.01)
(Continued)

(52) U.S. Cl.
CPC .............. *A61B 17/320725* (2013.01); *A61B 17/32037* (2013.01); *A61B 17/320758* (2013.01);
(Continued)

(58) Field of Classification Search
CPC ...... A61B 17/32037; A61B 17/320725; A61B 17/320758; A61B 2017/22069;
(Continued)

(56) References Cited

U.S. PATENT DOCUMENTS 3,730,185 A    5/1973    Cook et al.
4,739,760 A    4/1988    Chin et al.
(Continued)

FOREIGN PATENT DOCUMENTS

WO    01/35839 A2    5/2001
WO    2004/019816 A2    3/2004
(Continued)

OTHER PUBLICATIONS

EP Appln No. 12838492: Supplementary European Search Report dated Feb. 18, 2015.
(Continued)

*Primary Examiner* — Gregory Anderson
(74) *Attorney, Agent, or Firm* — Venable LLP; Michele V. Frank, Esq.

(57) ABSTRACT

Devices and methods are provided for percutaneously treating atherosclerotic plaques within blood vessels. Atherosclerotic plaques cause significant morbidity and mortality by narrowing the arteries, which adversely affects blood flow, and by acting as a source for thrombi and emboli thus causing acute organ ischemia. Current treatments include open surgery with its inherent drawbacks, and stenting, which is less invasive but leaves the plaque material in the artery, which promotes restenosis. The present invention combines the advantages of both approaches. In general, the invention provides tools that enable percutaneously dissecting the plaque from the arterial wall and removing it from the body.

31 Claims, 27 Drawing Sheets

(51) Int. Cl.
*A61B 17/3203* (2006.01)
*A61B 17/221* (2006.01)
*A61B 17/00* (2006.01)
*A61B 17/32* (2006.01)

(52) U.S. Cl.
CPC ........... *A61B 2017/00778* (2013.01); *A61B 2017/2212* (2013.01); *A61B 2017/2215* (2013.01); *A61B 2017/22052* (2013.01); *A61B 2017/22061* (2013.01); *A61B 2017/22069* (2013.01); *A61B 2017/320044* (2013.01); *A61B 2017/320741* (2013.01); *A61B 2017/320766* (2013.01)

(58) Field of Classification Search
CPC ........... A61B 2017/2215; A61B 2017/320044; A61B 2017/320741; A61B 2017/320766
See application file for complete search history.

(56) References Cited

U.S. PATENT DOCUMENTS

| | | | |
|---|---|---|---|
| 4,832,688 A | 5/1989 | Sagae et al. | |
| D307,323 S | 4/1990 | Scanlan | |
| 5,102,415 A | 4/1992 | Guenther et al. | |
| 5,653,726 A | 8/1997 | Kieturakis | |
| 5,728,123 A | 3/1998 | Lemelson et al. | |
| 5,782,840 A | 7/1998 | Nakao | |
| 5,782,848 A | 7/1998 | Lennox | |
| 5,851,226 A * | 12/1998 | Skubitz | A61N 1/056 607/126 |
| 5,906,622 A | 5/1999 | Lippitt et al. | |
| 5,947,985 A | 9/1999 | Imran | |
| 5,954,713 A | 9/1999 | Newman et al. | |
| 6,099,534 A * | 8/2000 | Bates | A61B 17/221 606/113 |
| 6,146,397 A | 11/2000 | Harkrider, Jr. | |
| 6,241,745 B1 | 6/2001 | Rosenthal | |
| 6,328,749 B1 | 12/2001 | Kalmann et al. | |
| 6,458,145 B1 * | 10/2002 | Ravenscroft | A61B 17/221 606/127 |
| 6,506,178 B1 | 1/2003 | Schubart et al. | |
| 6,565,583 B1 | 5/2003 | Deaton et al. | |
| 6,635,070 B2 | 10/2003 | Leeflang et al. | |
| 6,652,548 B2 | 11/2003 | Evans et al. | |
| 6,679,893 B1 | 1/2004 | Tran | |
| 6,695,858 B1 | 2/2004 | Dubrul et al. | |
| 6,719,775 B2 | 4/2004 | Slaker et al. | |
| 6,945,977 B2 | 9/2005 | Demarais et al. | |
| 7,108,704 B2 | 9/2006 | Trerotola | |
| 7,210,210 B2 | 5/2007 | Lippitt et al. | |
| 7,485,092 B1 * | 2/2009 | Stewart | A61B 17/00008 600/104 |
| 7,517,352 B2 | 4/2009 | Evans et al. | |
| 7,833,240 B2 | 11/2010 | Okushi et al. | |
| 7,955,350 B2 | 6/2011 | Konstantino et al. | |
| 8,012,117 B2 | 9/2011 | Bonnette et al. | |
| 8,057,496 B2 | 11/2011 | Fischer, Jr. | |
| 8,142,457 B2 | 3/2012 | Lafontaine | |
| 8,298,244 B2 | 10/2012 | Garcia et al. | |
| 9,017,328 B2 | 4/2015 | Bahney | |
| 9,216,034 B2 | 12/2015 | Avneri et al. | |
| 2002/0029052 A1 | 3/2002 | Evans et al. | |
| 2002/0082592 A1 | 6/2002 | Lary | |
| 2003/0120195 A1 | 6/2003 | Milo et al. | |
| 2004/0193204 A1 | 9/2004 | Lafontaine | |
| 2004/0199200 A1 | 10/2004 | Teague et al. | |
| 2006/0195137 A1 | 8/2006 | Sepetka et al. | |
| 2007/0208370 A1 | 9/2007 | Hauser et al. | |
| 2009/0099581 A1 | 4/2009 | Kim et al. | |
| 2010/0318178 A1 | 12/2010 | Rapaport et al. | |
| 2011/0144671 A1 | 6/2011 | Piippo Svendsen et al. | |
| 2013/0317515 A1 | 11/2013 | Kuroda et al. | |
| 2014/0128894 A1 | 5/2014 | Sepetka et al. | |
| 2014/0276809 A1 | 9/2014 | Smith et al. | |
| 2014/0296889 A1 | 10/2014 | Avneri et al. | |
| 2014/0364868 A1 | 12/2014 | Dhindsa | |
| 2015/0066047 A1 | 3/2015 | Chu et al. | |
| 2015/0119896 A1 | 4/2015 | Krolik et al. | |
| 2015/0342624 A1 | 12/2015 | Lippitt et al. | |

FOREIGN PATENT DOCUMENTS

| | | |
|---|---|---|
| WO | 2009/120205 A1 | 10/2009 |
| WO | 2013050880 A2 | 4/2013 |

OTHER PUBLICATIONS

PCT/IB2012/002847: International Search Report and Written Opinion, dated Apr. 29, 2013.

Holzapfel et al., "Anisotropic Mechanical Properties of Tissue Components in Human Atherosclerotic Plaques," Journal of Biomedical Engineering, 2004; 126:657-665.

Scholtes et al., "Subintimal Angioplasty Track of the Superficial Femoral Artery a Histological Analysis," Circ. Cardiovasc. Interv. 2012; 5:e6-e8.

Sobieszczyk, MD Piotr, "Catheter-Assisted Pulmonary Embolectomy", Circulation. 2012;126:1917-1922.

International Search Report and Written Opinion in corresponding International Application No. PCT/IB2016/000891, dated Sep. 20, 2016.

Office Action in corresponding U.S. Appl. No. 15/167,629, dated Sep. 28, 2016.

European Office Action issued in European Application No. 12838492.2 dated Dec. 22, 2017 (3 pages).

* cited by examiner

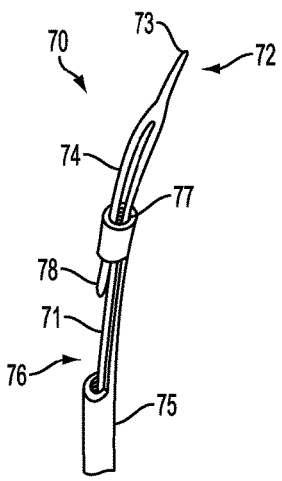
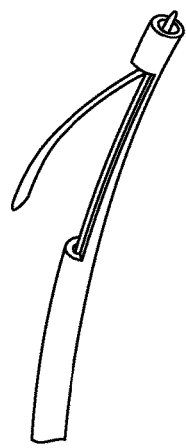
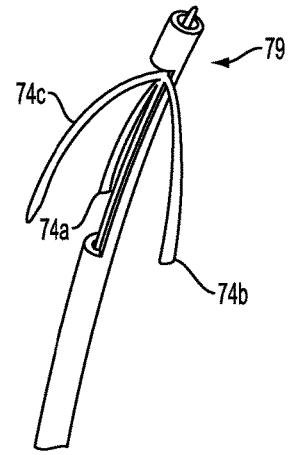
FIG. 10AA     FIG. 10BB     FIG. 10CC
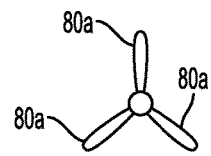 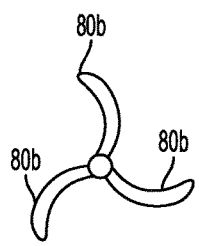 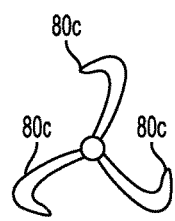
FIG. 10A     FIG. 10C     FIG. 10E
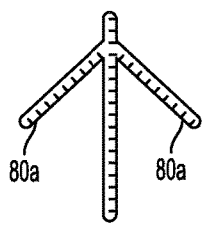 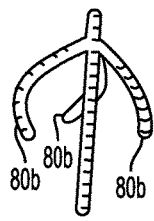 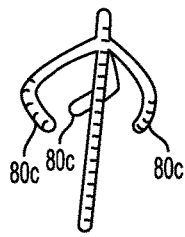
FIG. 10B     FIG. 10D     FIG. 10F

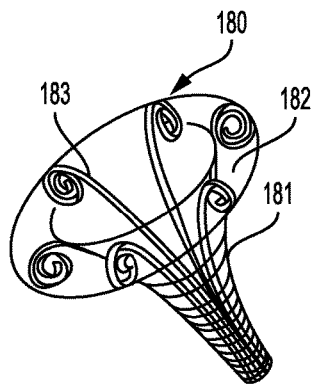
FIG. 18A
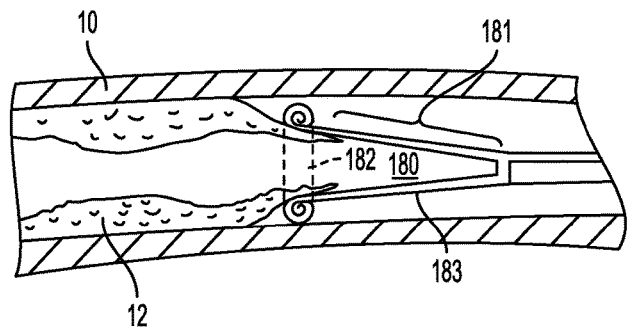
FIG. 18B
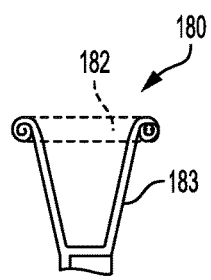 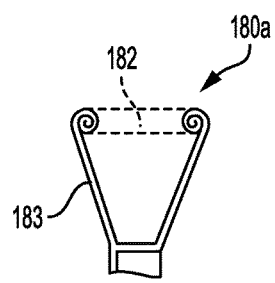 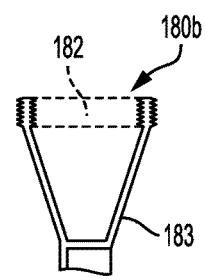 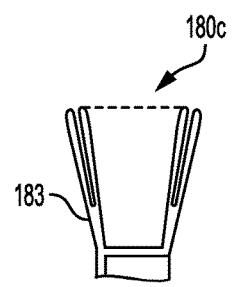
FIG. 18C    FIG. 18D    FIG. 18E    FIG. 18F

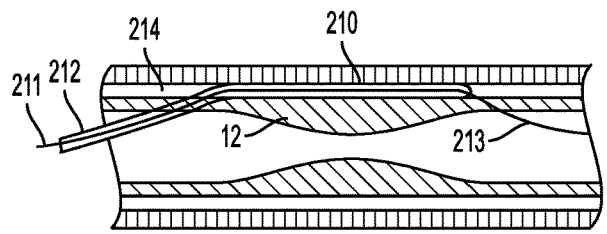 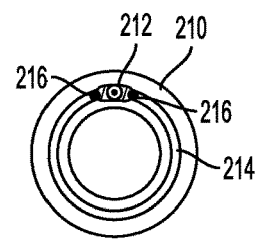
FIG. 22A  FIG. 22B
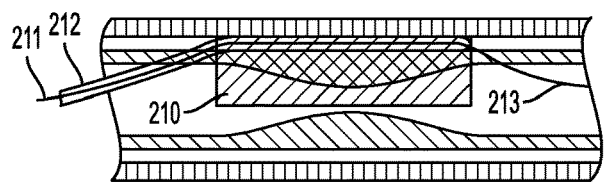 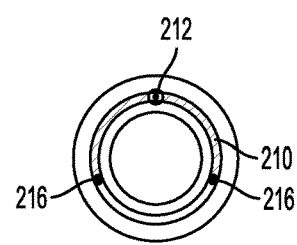
FIG. 22C  FIG. 22D
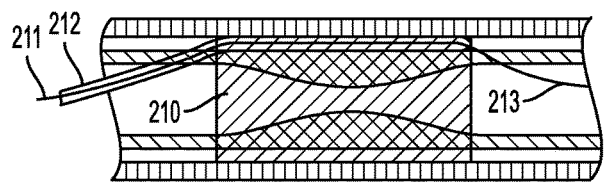 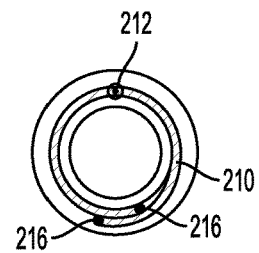
FIG. 22E  FIG. 22F
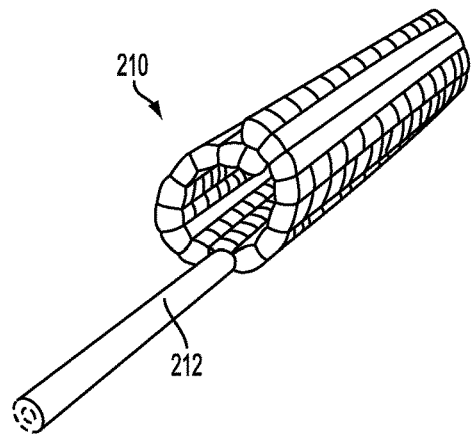
FIG. 23

DEVICES AND METHODS FOR PERCUTANEOUS TISSUE REMOVAL

CROSS-REFERENCE TO RELATED APPLICATIONS

This application is a U.S. National Phase Application of International Application No. PCT/IB2012/002847, which has an international filing date of Oct. 4, 2012, and which claims priority to U.S. Provisional Application No. 61/542,901, filed Oct. 4, 2011, the disclosures of which are incorporated by reference in their entirety.

FIELD OF THE INVENTION

The present invention relates to devices and methods for percutaneously treating atherosclerotic plaques within blood vessels.

BACKGROUND OF INVENTION

The normal human artery is composed of three main layers. The innermost layer lining the artery, in contact with the blood, is the intima. This is a single cell layer of endothelial cells, which among other functions regulates vascular tone, platelet activation and thrombus formation, monocyte adhesion and inflammation and vascular remodeling. The media—the middle layer, consists of several layers of smooth muscle cells and elastic fibers. The outermost layer is the adventitia, which is mainly composed of connective tissue containing small blood vessels and nerves.

Atherosclerosis is one of the major causes of cardiovascular cerebrovascular and peripheral vascular morbidity and mortality. It is a disease of large and medium-sized muscular arteries, which is characterized by the formation of discrete lesions called atherosclerotic plaques, or atheromas, thought to be caused by injury to the endothelium. An atheroma is a buildup of lipids, cholesterol, calcium, and cellular debris within the intima of the vessel wall. Atherosclerotic buildup also results in vascular remodeling, acute and chronic luminal obstruction, abnormalities of blood flow and diminished oxygen supply to target organs.

A complex and incompletely understood interaction is observed between the critical cellular elements of the atherosclerotic lesion. These cellular elements include endothelial cells, smooth muscle cells, platelets, and leukocytes.

The presence of risk factors accelerates the rate of development of atherosclerosis. The main risk factors for the development and progression of atherosclerosis include hyperlipidemia and dyslipidemia, hypertension, cigarette habituation, air pollution, diabetes mellitus, older age, male sex, family history of premature CAD, obesity and physical inactivity. Additional risk factors associated with atherosclerosis include various metabolic diseases, autoimmune diseases, chronic kidney disease, and depression.

Manifestations of atherosclerotic disease depend on the affected organs and the type of lesions. Chronically narrowed arteries give rise to symptoms of insufficient blood flow such as angina pectoris (chest pain during exertion), intermittent claudication (leg pain during exertion), and chronic leg ulcers. Acute events can occur as a result as of plaque rupture and thrombosis, which might totally clog the artery as in most cases of acute myocardial infarction (heart attack), or as a result of distal embolization of plaque fragments, as in many cases of stroke.

Treatment of atherosclerosis depends on many factors including the location of symptomatic lesions, the severity of symptoms, and their dynamics.

Acute obstruction events usually require acute intervention. For acute coronary events, treatment is urgent percutaneous angioplasty (balloon dilation of the obstructed artery) and stenting. Depending on the time from the beginning of symptoms, acute ischemic stroke is sometimes treated urgently by percutaneous mechanical removal of the obstruction or injection of compounds that lyse it (tPA, streptokinase), but in many such cases treatment will only focus on the prevention of future events. Acute limb ischemia is also treated by urgent revascularization, either percutaneous or surgical.

The treatment of chronic obstruction is usually a combination of medical therapy and an interventional procedure.

Medical treatment may include anti platelet agents such as Aspirin, anti-coagulants such as Coumadin, Statins, which decrease cholesterol levels and stabilize plaques, and more.

Interventional procedures may be surgical or percutaneous and are aimed at revascularization of the target organs and removal of a potential source of emboli, if present.

Surgical treatments include bypass surgery, more commonly used for coronary and lower limb arteries, and endarterectomy, which is used for limb and carotid arteries, and involves opening the artery and removing the plaque along with the intima. Obviously, the disadvantage of surgery is its highly invasive nature, the need for anesthesia, and the pain and stress involved which make it unsuitable for certain patients.

Percutaneous procedures enable treating the lesions using long catheters inserted to the arteries at a distant point such as the groin arteries. The most common of these is placement of a stent, a metal structure which is inserted to the artery in a closed state and expanded within the lesion so as to keep the lumen patent. This can be done with or without balloon angioplasty (inflation of a balloon in the lesion to enlarge the lumen prior to or following stent placement). The main disadvantage of angioplasty and stenting is that the plaque remains in the artery. This has several deleterious consequences. First—in carotid stenting, many of the post stenting strokes are caused not during the procedure, but after it, and are probably related to plaque material squeezing through the cells of the stent and embolizing to the brain (a phenomenon known as the "mashed potato effect"). Second—in many cases the plaque encroaches on the stent and does not enable attainment of a normal vascular lumen. This in turn affects flow dynamics and shear stress, which may enhance atherogenesis and cause restenosis. Third—the plaque material itself contains many inflammatory and prothrombotic substances. This may be the reason for the high rate of restenosis experienced after stenting.

In view of the disadvantages of surgery and of stenting, and for treating heavily calcified lesions, novel procedures have been developed that attempt to remove the plaque via a percutaneous route. This type of procedure is termed percutaneous atherectomy, and utilizes some form of ablation device that removes plaque from within the lumen. Examples of such devices based on mechanical grinding include the SILVERHAWK directional atherectomy device (Covidien), the ROTABLATOR rotational atherectomy device (Boston Scientific), the JETSTREAM NAVITUS (Pathway Medical Technologies). Other systems use different forms of energy for removing plaque material such as in laser atherectomy.

The two major drawbacks of these devices are:

(1) It is impossible to know exactly how much plaque to remove—too much will injure the artery with possible rupture or dissection in the wall, too little will leave a significant amount of atheroma. Angiography is not accurate enough for this purpose, ultrasound is being incorporated in such systems but will never allow as accurate a result as that achieved with endarterectomy.

(2) Its fibrous cap having been removed, the atheroma with its deleterious contents is left exposed to the blood flow.

Two other methods worthy of mention are subintimal angioplasty and remote endarterectomy. Although good results were reported with both methods, they require high technical proficiency, have a long learning curve, and have therefore not gained much acceptance in the medical community.

Subintimal angioplasty (also known as the Bolia technique) is a percutaneous procedure developed for treating chronic total occlusions (CTOs), in which the obstruction of the lumen is complete, and the system cannot traverse the lesion. In these cases, a guidewire is directed into the subintimal space between the intima and the media of the arterial wall, and passed across the lesion until it re-enters the lumen beyond it. Angioplasty and stenting is then performed in this new artificial channel within the arterial wall. As the atheroma is still adjacent to the stent, the disadvantages mentioned above for regular stenting apply here as well.

Remote endarterectomy is an open vascular procedure performed on the arteries of the thigh, and mainly used to remove long, severe plaques. The artery is surgically exposed and cut open, and the dissection plane between the intima and media is identified. Special tools for separating the plaque from the arterial wall are inserted around the "core" which is subsequently removed. This procedure is by definition a surgical one and the tools are not appropriate for percutaneous use. Results of this procedure are very good compared to other treatment modalities, and advantages include decreased morbidity and shorter hospital stays compared to surgery, preservation of bypass options, and decreased incidence of limb-threatening ischemia when a remote endarterectomy fails.

It is clear from the above, that percutaneous procedures and devices enabling subintimal removal of atherosclerotic plaques could provide great advantages over current practice, by combining the accuracy of surgical endarterectomy with the benefits of minimally invasive procedures. The aim of the current invention is to describe such a solution, which will also be simple, safe, and effective.

SUMMARY OF INVENTION

The invention includes various solutions to the removal of atherosclerotic plaque from arteries. The apparatus and methods include use of the natural dissection plane between the plaque and the media of the artery.

Embodiments of the present invention include devices and methods removal of atherosclerotic plaque from arteries, in particular for percutaneous endarterectomy.

One embodiment of the invention is a device for percutaneous endarterectomy including: a shaft configured to pass through the lumen of a catheter, having a distal end; and one or more expandable fingers having a proximal and distal end with the proximal end of the one or more fingers attached to the distal end of the shaft. In that embodiment, the fingers are configured to remove an atherosclerotic plaque by peeling the plaque at the subintimal space without performing an incision into the intimal space and without use of a blade. Furthermore, optionally, the finger may be configured so that radial force applied by the fingers decrease going from the proximal to the distal end of the tip relative to the plaque.

The device may further include a catheter having a lumen and a distal end configured so that the shaft passes through the lumen of the catheter.

This embodiment of the invention may have various other features including but not limited to one or more of the following: a) the one or more fingers are connected to each other by one or more spokes; b) a distal end of the one or more expandable fingers, when expanded, are substantially parallel to the shaft; c) the one or more fingers are self-expanding; d) the one or more fingers include a plurality of fingers to surround the shaft; e) the one or more fingers include a substantially cylindrical formation when expanded; f) the one or more fingers include a substantially conical formation when expanded; g) the one or more fingers are elongated and form a ribbon-shaped configuration; h) the one or more fingers are each connected to a spoke, each spoke is connected to a rod and the shaft includes a lumen through which the rod may pass; i) the one or more fingers have a guidewire for passing a guidewire therethrough; j) the one or more fingers are held in a position relative to the shaft by a spoke; k) the one or more fingers are held in a position substantially parallel to the shaft; l) the one or more fingers are substantially straight; m) the one or more fingers are substantially curved; n) the one or more fingers have a bent end; o) the one or more fingers have a transverse cross-section with a leading end and an trailing end, wherein the leading end is smaller than the trailing end; p) the one or more fingers has a longitudinal length and a cross-section size of the one or more fingers along the longitudinal length varies; q) the one or more fingers may have the same or different cross-sectional shapes; r) the one or more fingers include a loop; s) the one or more fingers are petal-shaped; and/or t) the one or more fingers include a plurality of fingers surrounding the shaft and the plurality of fingers, when expanded, are spaced apart from each other. The fingers may also be rotatable.

Another embodiment of the invention is a device for percutaneous endarterectomy including: a rod; a shaft having a lumen and a distal end for passing over the rod; a catheter having a lumen and a distal end for passing over the shaft; one or more expandable and rotatable fingers having a proximal and distal end with the proximal end of the one or more fingers attached to the distal end of the shaft, having an exterior surface facing the artery and an interior surface facing the rod; and one or more spokes connecting the rod to the one or more expandable fingers on the interior surface whereby the fingers are controllable by the rod through the one or more spokes, whereby the fingers are configured to remove an atherosclerotic plaque by peeling the plaque at the subintimal space without performing an incision into the subintimal space and without use of a blade, whereby the distal end of the expandable fingers when expanded is parallel to the shaft, and whereby the fingers are configured to be advanced forwards and/or backwards.

In one embodiment, the fingers are configured so that radial force applied by the fingers decrease going from the proximal to the distal end of the tip relative to the plaque. In another embodiment, the fingers further include a centerline running longitudinally from the distal end of the fingers to the proximal end of the fingers. Optionally, the fingers also further include a marker at the distal end of the centerline. The fingers may be radially expandable.

Two or more rows of spokes may connect the rod to the one or more fingers. In one embodiment, the two or more rows of spokes are parallel to each other. In another embodiment, the two or more rows of spokes create a parallelogram configuration with two sides of the parallelogram formed by the rows of spokes, one side formed by the shaft and the other side formed by the one or more fingers.

In any of these embodiments, the distal tip of the fingers may be sharp and the distal end of the fingers is sufficient to find the edge of the plaque without cutting the media or adventitia. Alternatively, in any of these embodiments, the distal end of the fingers is blunt and sufficient to find the edge of the plaque without cutting the media or adventitia.

The device for percutaneous endarterectomy of the invention may further include additional components such as e.g. a dissector, cutting tool and/or rotatably mounted jets.

The dissector may include expandable loops configured to separate the plaque from the arterial wall around its circumference and along its whole length. In one embodiment, the dissector is configured for passing through the lumen of a catheter. In another embodiment, a cutting tool located at the tip of the dissector tool. The dissector tool may also include one or more jets.

In addition, when jets are included the device includes monitoring of pressure. Thus, in one embodiment, the fluid pressure of liquid injected by the one or more jets and the net volume of liquid injected is monitored. In another embodiment, the pressure inside the catheter is monitored. In yet another embodiment, the pressure inside the artery is monitored.

In one embodiment, the device includes a cutting tool. A suitable cutting tool is a cutting tool having one or more deployable angled blades at the tip of the cutting tool. In one embodiment, the cutting tool is configured so that the deployable angled blades excise the plaque.

In addition to the cutting tool, the device may also include a funnel shaped catheter tip. This funnel shaped catheter tip may be advanced around the plaque to collect plaque after cutting.

In another embodiment, the devices also include one or more rotatably mounted jets. In one embodiment, the jets are configured to sever the plaque from the vascular walls.

The devices may also contain a balloon and/or cage configured to separate the plaque.

Another embodiment of the invention is a device for percutaneous endarterectomy including: a shaft; a catheter having a lumen and a distal end for passing over the shaft; one or more expandable and rotatable retrograde fingers having a proximal and distal end with the proximal end of the one or more fingers attached to the distal end of the shaft wherein the distal end of the fingers faces the proximal end of the catheter; a slideable sheath positioned on the distal end of the catheter configured to cover the one or more rotatable fingers, wherein the fingers are configured to remove an atherosclerotic plaque by peeling the plaque at the subintimal space without performing an incision into the subintimal space and without use of a blade. This device may be configured so that sliding of the sheath expands the fingers. In one embodiment, the fingers remove the plaque by a backward motion.

The devices of the invention may be used in methods of percutaneous endarterectomy. Thus, other embodiments of the invention are method of percutaneous endarterectomy which use of the devices of the invention, whereby an atherosclerotic plaque is removed by peeling the plaque at the subintimal space without performing an incision into the subintimal space and without use of a blade.

Another embodiment of the invention is a method of percutaneous endarterectomy including: accessing an artery having an atherosclerotic plaque nearby the plaque with a device including: a shaft configured to pass through the lumen of a catheter, having a distal end, and one or more expandable fingers having a proximal and distal end with the proximal end of the one or more fingers attached to the distal end of the shaft, wherein the fingers are configured to remove an atherosclerotic plaque by peeling the plaque at the subintimal space without performing an incision into the subintimal space and without use of a blade, wherein the distal end of the expandable fingers when expanded is substantially parallel to the shaft; peeling the plaque at the subintimal space without performing an incision into the subintimal space and without use of a blade; and separating the plaque from the arterial wall around its circumference and along its length.

The method may further include cutting the intima connecting the distal part of the plaque to the arterial wall and optionally local treatment of the exposed media after cutting by instillation of endothelial progenitor cells, stem cells, other cells, or substances. In one embodiment of the method, the step of cutting comprises use of a dissection tool having one or more deployable angled blades. Via use of the angled blades, the step of cutting my include cutting the intima and excises the plaque without leaving an intimal flap. The method may further include removal of the cut plaque (via e.g. use of a funnel shaped catheter tip) and removal of the device. The step of separating the plaque may include use of a dissector. The method may optionally include the step of locating the plaque prior to peeling. In one embodiment, step of locating includes moving the fingers of the device along the subintimal space to locate the plaque.

Another embodiment of the invention is a device for entry into subintimal space having: a rotatable shaft having a metal strip attached to the distal tip of the shaft, wherein the distal end of the metal strip curves; one or more inclined blades attached to the distal end of the metal strip; a removable sheath for sliding over the rotatable shaft and for covering the one or more inclined blades; a catheter having a lumen and a distal end for passing over the shaft; and one or more balloons disposed towards the distal end of the catheter; wherein the device is configured so that rotation of the shaft rotates the blades which in turn cuts through the intima, wherein the sheath is configured to be removable during use of the device.

Yet another embodiment of the invention is a device for percutaneous endarterectomy including: a catheter having a lumen; one or more guidewires for threading through the subintimal space, wherein the guidewires pass through the lumen of the catheter; an expandable separator device comprising a hollow cylinder folded onto an elongated member, wherein the separator when deployed assumes a cylindrical shape with an overlap of both ends over the slit. In one embodiment, the expansion of the separator device separates the plaque from the arterial wall. The device may also further include a cutting tool.

In certain embodiments, the devices of the invention include a grinder. The grinder may be mounted on the distal end of the catheter. Alternatively, the grinder may be deployable through the lumen of the catheter.

Yet another embodiment of the invention is a device for percutaneous endarterectomy including: a catheter having a lumen and a distal end; one or more guidewires for threading through the subintimal space, wherein the guidewires pass through the lumen of the catheter; a shaft having a distal end passing through the catheter lumen; one or more expandable loop shaped wings having a distal edge and a distal tip, wherein the loop shaped wings are attached to the shaft; a removable cap on the distal end of the catheter, whereby the device is configured so that removal of the cap causes expansion of the wings. The cap may include a tip and a shaft, such that the shaft of the cap passes through the catheter lumen. The device may also include a web covering the one or more wings: In one embodiment, the web is configured to be an emboli protection device. Additionally, the device may further include a cutting tool. In one embodiment, the one or more wings are configured to anchor the distal intima and to thereby enable cutting without leaving an intimal flap.

Yet another embodiment of the invention is a device for inserting one or more guidewires into a subintimal space of an artery including: a catheter having a lumen, a distal end and a tip at the distal end; a pushing element at the tip of said catheter; a balloon proximal to said pushing element; and one or more guidewire catheters adjacent and parallel to said catheter, said guidewire catheter passing over balloon and configured to assume an orientation essentially parallel to longitudinal axis of distal catheter or up to approximately 5 degrees outward of said axis. The pushing element may be a balloon or include an expandable metal element. In one embodiment, the balloon is moveable relative to said catheter.

This device for inserting one or more guidewires into a subintimal space of an artery may be used in a method for inserting one or more guidewires into subintimal space including identifying a lesion, bringing the device proximate to lesion, inflating proximal balloon, applying tension by the pushing element, and pushing guidewire forward into subintimal space. The method may further include one or more of (a) application of suction on the area between the proximal and distal balloon prior to the pushing the guidewire into subintimal space and (b) verification of guidewire insertion into subintimal space by use of angiography.

In another embodiment, this device for inserting one or more guidewires into a subintimal space of an artery may be used in a method for removal of a plaque including inserting one or more guidewires using the device and rotating the one or more guidewires around the plaque, first forward until the one or more guidewires re-enter the lumen and then backwards to remove the plaque.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE FIGURES

The accompanying drawings, which are included to provide a further understanding of the invention and are incorporated in and constitute a part of this specification, illustrate preferred embodiments of the invention and together with the detailed description serve to explain the principles of the invention. In the drawings:

FIGS. 10AA, 10BB, 10CC and 10A-F show various overall shapes of a distal end of a fingered shaft (edger) from both side and end views in accordance with the principles of the invention.

FIG. 18A-C show an embodiment of a dissector tool in three dimensional and longitudinal sections.

FIG. 18D-F show longitudinal sections of alternative embodiments of dissector tools.

FIG. 22A-F shows stages of use of a medial plaque remover device.

FIG. 23 shows an embodiment of a medial plaque remover device in its inflated position.

DETAILED DESCRIPTION OF THE EMBODIMENTS

The invention includes various solutions to the removal of atherosclerotic plaque from arteries. This invention includes methods and devices for performing percutaneous endarterectomy (i.e. removal of atherosclerotic plaques from arteries via a e.g. a catheter). The devices and methods may release plaque at its edge and peel away the plaque naturally, preferably, for example, along the subintimal space. All may be preferably based on the same principle of utilizing the natural dissection plane, which in the subintimal space, exists between the plaque and the media of the artery, for removing the plaque with a percutaneous tool.

As known to those skilled in the art, the subintimal space is a potential space where a false lumen could form if blood flow were to enter it through an intimal tear and cause an arterial dissection.

It is the same space used for passing the guidewire and creating an artificial extraluminal route in subintimal angioplasty procedures (the Bolia technique), and where the plaque is usually separated from the arterial wall in open endarterectomy operations. A recent article reports a case in which an occluded artery was endarterectomised two months after a subintimal angioplasty was performed on it, and histological cuts demonstrated that "the subintimal track had been formed between the internal elastic lamina and the atherosclerotic plaque at most levels." Scholtes et al., "Subintimal Angioplasty Track of the Superficial Femoral Artery: A Histological Analysis", *Circ Cardiovasc Interv.;* 2012; 5:e6-e.8. It is therefore thought that subintimal angioplasty is not a random extraluminal revascularization procedure but creates subintimal passage in the form of a dissection between the atherosclerotic plaque and the media of the artery." Scholtes et al.

In this invention, the plane between the media and intima is utilized because it may be the pathway of least resistance around the plaque. As such, the guidewire in subintimal angioplasty procedures usually finds its way into the subintimal space quite naturally. The current invention describes additional ways in which to enter this space.

Figure 1A:
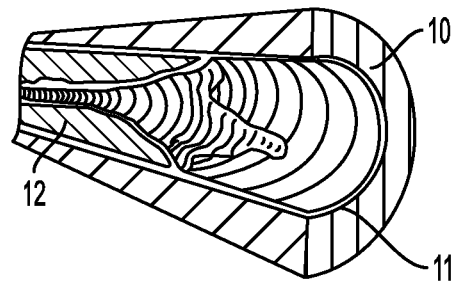
FIGS. 1A-B show two different common structures of the edge of an atherosclerotic plaque in an artery.
Figure 1B:
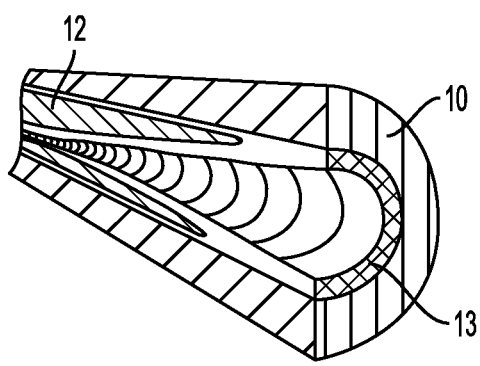

FIGS. 1A-B show two different common structures of the edge of an atherosclerotic plaque in an artery. With reference to FIG. 1A the artery comprises normal media 10 and normal intima 11. The atherosclerotic plaque 12 in the artery is shown in both FIG. 1A and FIG. 1B. FIG. 1B also illustrates the atherosclerotic (thickened) intima 13.

Two general directions are described, which differ in the aspect from which the plaque is approached: its edge or the medial aspect.

"Plaque's edge," as used herein refers to the border of the occluding lesion, whether proximal or distal. In some cases, as shown in FIG. 1A, the lesion may have a distinct, abrupt border between a normal or essentially normal area and a stenotic area, wherein an actual "step" in thickness of the intima is present. In other cases, this border may be less distinct, with a gradual transition or tapering between the stenotic and patent areas of the artery (FIG. 1B). In such cases, the "edge" would be a location initially chosen by the physician, from which the stenosis is deemed of no clinical significance.

"Medial aspect" refers to an approach to the plaque beginning with passage of a device in the subintimal space throughout the length of the lesion.

All the described procedures and tools are preferably used after deployment of an embolic protection device in the artery. Alternatively, by way of example, the treated area may be isolated by inflating balloons at one or both of its ends.

The tools and methods described herein may be used with slight modifications either in an antegrade or in a retrograde fashion. Antegrade use refers to advancement around the plaque while the device is being pushed forward. This has the advantage of not necessitating traversing of the lesion before initiation of treatment; hence, it is appropriate for the treatment of CTO lesions (Chronic Total Occlusions). The disadvantage is that pushing the device forward may be more difficult technically than pulling it. Retrograde use refers to advancement around the plaque while the device is being pulled backward. This requires that the device be passed through the lesion prior to initiation of treatment. Only then can it be deployed and pulled back. The main disadvantage is that the lumen through some lesions may be so stenotic as to prevent passage of the catheter, in which case this approach cannot be used. On the other hand, this approach may be more suitable for lesions at bifurcations.

After placing the treatment catheter at the vicinity of the lesion, demonstrating it, optionally placing any of the many available embolization protection devices, and anchoring the treatment catheter, treatment may follow these stages:

1. Access into the subintimal space. This entails passage of an instrument into the subintimal space ("SIS"), and in some cases initial separation of the plaque, a process herein referred to as "edging," which may be performed using an "edger" tool. Such separation is intended to enable further separation of the plaque from the arterial wall, herein referred to as "dissection."

2. Dissection of the plaque. This entails separation of the plaque from the arterial wall around its circumference and along its whole length. Dissection may be performed using a specialized "dissector" tool, or in some embodiments with the edger tool.

3. Distal cutting. After the plaque was separated all around, the intima connecting the distal part of the plaque to the arterial wall may be cut.

4. Closure. A device enclosing the plaque is generally closed so as to contain the plaque and its fragments.

5. Removal. The device with the plaque in it is removed from the artery.

6. Medial surface treatment. Optionally, treatment may be applied that enhances arterial healing and attenuates thrombogenicity and platelet adhesion to the exposed medial surface. Such treatment may consist of re-endothelialization therapy by e.g. instillation of endothelial progenitor cells, stem cells, or other cells or substances. Typically, such treatment will be applied using a specially designed balloon catheter system which keeps the cells/substance in contact with the arterial wall while at the same time allowing continuous blood flow through the treated area.

The tools and methods described herein are aimed at removal of the plaque as a whole, preferably in one piece. For example, the exemplary devices and methods described herein provide for release of the plaque, preferably at its edge, and peeling of the plaque. A different approach is to use a grinder/macerator tool, which can also be used along with certain aspects and embodiments of the current invention. However, such a tool adds complexity, cost, and danger to the system, and in addition, grinding the plaque releases various deleterious thrombogenic and inflammatory substances into the blood stream, hence the preference for removal of the plaque without disintegrating it.

Most preferred embodiments of the invention are based on the approach of attacking the plaque from its edge. In particular, the devices and methods of the invention provide for release of the plaque, such as through scraping and peeling of the plaque. Preferably, this is done without making a cut into the intima and/or media. Without radial cutting, grinding or abrading the plaque as the primary removal technique, the plaque may be scraped or edged away from the vessel wall to be peeled away along the natural dissection plane. In one embodiment, a device, utilizing, for example, fingers or projections, approaches the plaque from inside the vessel to contact and/or engage the plaque with a scraping action, for example, to find the way into the subintimal space. With the scraping action, the plaque/intima layer separates because the plaque/intima is naturally peeled away. The methods and devices of the invention do not rely e.g. on radial cutting, grinding, or abrasion and as such are much more gentle.

Figure 2A:
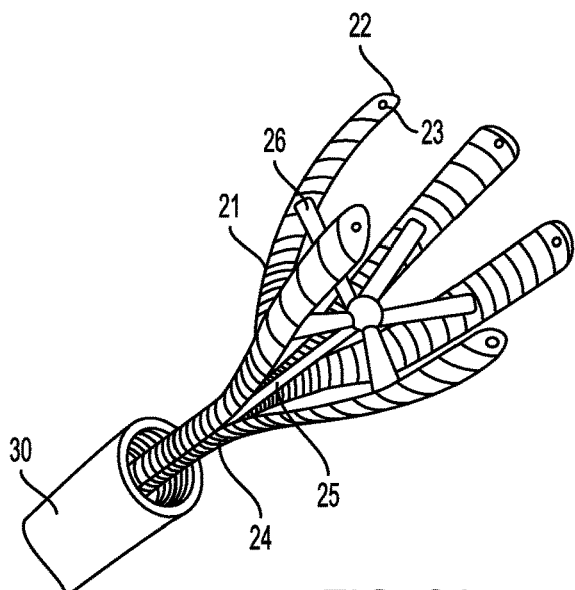
FIGS. 2A-F show embodiments of edger tools in accordance with the principles of the invention.
Figure 2B:
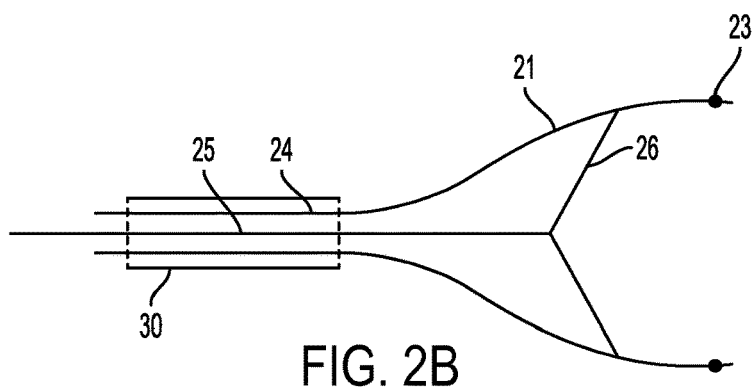
Figure 2C:
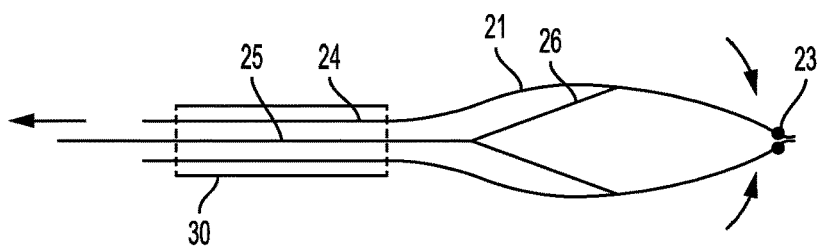

In a preferred embodiment, an edger tool is provided including a tubular member from which end extend several elongated radially expandable "fingers." An example of such tool based on an umbrella like mechanism is shown in FIG. 2A-2E. FIG. 2A is a three-dimensional depiction of edger 20 which is passed through catheter 30. It includes of shaft 24 from which extend fingers 21. Rod 25 extends through shaft 24 and is connected to each finger 21 by spoke 26. At centerlines 22 of fingers 21 near their edge may be additionally installed radiopaque marker 23. A longitudinal section of edger 20 in its open position is shown in FIG. 2B and in its closed position in 2C. Fingers 21 may be formed of an elastic material and pre-shaped in the open position, such that when pushed out of guiding catheter 30 and in the absence of pulling resistance by rod 25, the edger will open. In such case, release of rod 25 controls the degree of finger 21 radial expansion and open diameter. Alternatively, finger 21 radial expansion may depend on pushing rod 25 forward. In any case, following radial expansion, fingers 21 assume a position essentially parallel to that of shaft 24 longitudinal axis (FIG. 2B).

Figure 2D:
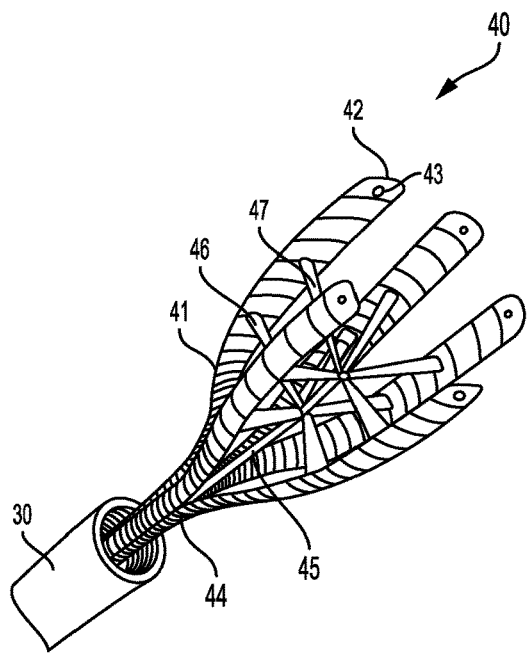
Figure 2E:
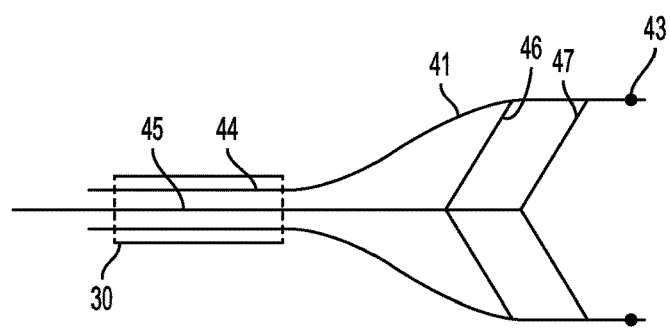
Figure 2F:
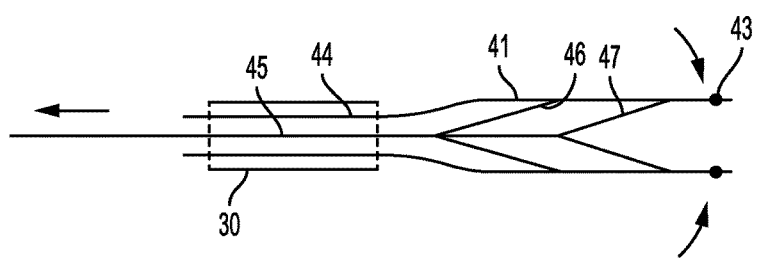

A slightly different example of edger tool is shown in FIG. 2D-2F. This tool is similar to edger 20 but has additional spokes intended to maintain the fingers' parallel position. More particularly, FIG. 2D is a 3D depiction of edger 40 which is passed through catheter 30. It includes shaft 44 from which extend fingers 41. Rod 45 extends through shaft 44 and is connected to each finger 41 by inner spoke 46 and a more distal outer spoke 47. Inner spoke 46 and outer spoke 47 are of the same length, and the distances between their connection points on finger 41 and on rod 45 are also equal, such that they form a parallelogram. At centerlines 42 of fingers 41 near their edge may be additionally installed radiopaque marker 43. A longitudinal section of edger 40 in its open position is shown in FIG. 2E and in its closed position in 2F. Fingers 41 may be formed of an elastic material and pre-shaped in the open position, such that when pushed out of guiding catheter 30 and in the absence of pulling resistance by rod 45, the edger will open. In such case, release of rod 45 controls the degree of finger 41 radial expansion and open diameter. Alternatively, finger 41 radial expansion may depend on pushing rod 45 forward. In any case, following radial expansion, fingers 41 assume a position essentially parallel to that of shaft 44 longitudinal axis (FIG. 2E), which is maintained at any opening diameter due to the parallelogram design.

In one embodiment, the fingers 41 are of the same length. The fingers are designed so that radial force applied by the fingers decrease going from the proximal to the distal end of the tip (relative to the plaque). Thus, in one embodiment, the fingers deliver more force on the proximal end of the finger and less force on the distal end. In one embodiment, the tips of fingers are parallel to the shaft so that they do not cut the artery and so they are substantially in the direction of the dissection plane. The fingers are also so configured that they are more rigid towards the distal end and more flexible to the distal end. Furthermore, the edges of the fingers may be blunt or rounded. Thus, in one embodiment, the radius at the end of the fingers is not sharp, rather it is blunt and sufficient to find the edge of the plaque without cutting the intima. The fingers, in this configuration, may be used to remove the plaque in a forward motion. In one embodiment, the longitudinal sections of the fingers are parallel. It is thought that less force on the distal end results in a device that provides for a more gentle removal of the plaque and the ability to find the natural separation of the plaque. The embodiments shown and described herein are exemplary. For example, the force differences can be achieved in a variety of ways including structurally (via e.g. use of structural features such as struts and guidewires or a changing cross-section) or functionally (via e.g. use of a different materials).

Fingers 41 as shown in FIG. 2A have a thin configuration that may be flat or curved as desired in accordance with the principles of the invention. Although other configurations may be used in accordance with the principles of the invention, for example, the lateral and transverse cross-sections of finger 41 may vary, and, further may vary, for example, as discussed in other embodiments described herein. Finger cross-sections also are shown in FIGS. 10G-K.

Figure 3A:
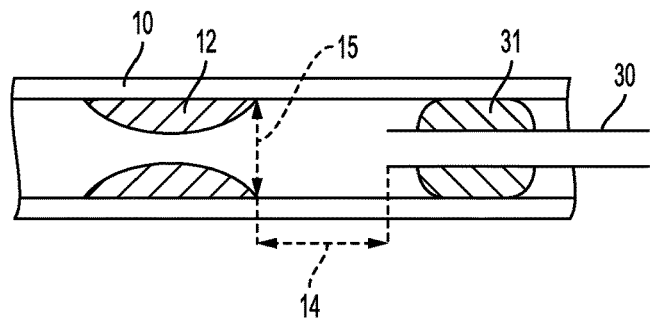
FIGS. 3A-3E show stages of use of an edger tool in accordance with the principles of one embodiment of the invention.
Figure 3B:
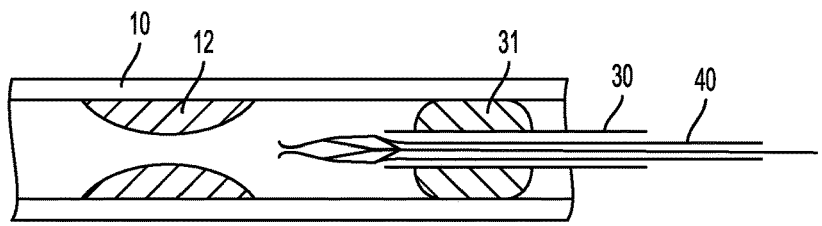
Figure 3C:
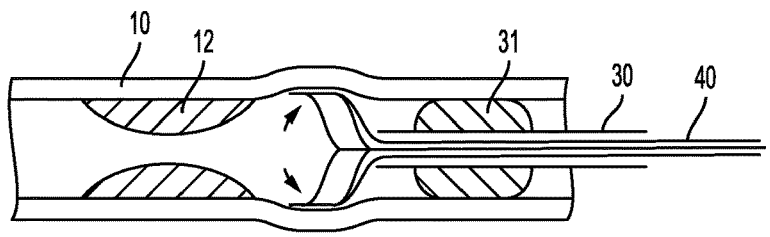
Figure 3D:
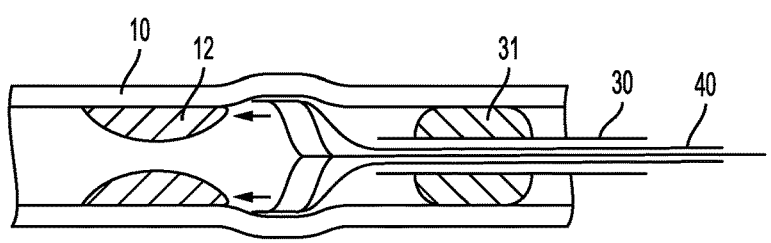
Figure 3E:
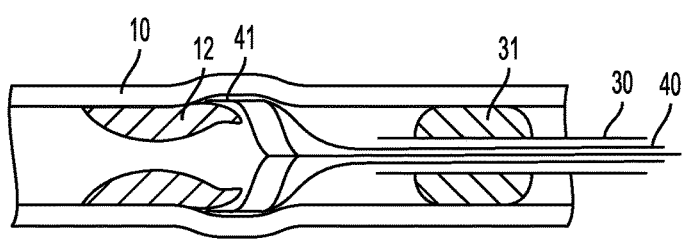

In another embodiment, the fingers may be sharp and the fingers are configured to find the edge of the plaque without radially cutting the intima. In another embodiment, due to the lateral positioning of the edger relative to the plaque, the fingers, may be relatively blunt, sharp or otherwise in accordance with the principles of the invention to accomplish the scraping and/or edging of the plaque so it may be removed along its natural dissection line. The fingers of the edger tools in accordance with the principles of the invention may be caused to probe along the arterial wall to find the edge and/or natural line/plane of dissection of the plaque. In one embodiment, the fingers press gently against the arterial wall and gently scrape the plaque to find the edge and/or natural separation. FIG. 2A-3E show the stages of edger 40 use. More particularly FIG. 3A shows longitudinal section of artery having inner diameter 15 with media 10 and plaque 12 at a distance 14 from tip of catheter 30, which is anchored by balloon 31. FIG. 3B shows edger 40 in its closed position passed through catheter 30. FIG. 3C further shows edger 40 in its open position. FIG. 3D shows the above with edger 40 being advanced towards plaque 12. FIG. 3E further shows fingers 41 separating between media 10 and plaque 12. The distal portions of the fingers may also be substantially parallel to the central axis of the device e.g. pushing rod In use, guiding catheter 30 is brought to the vicinity of the target lesion 12 which is then demonstrated angiographically. If possible, an embolization protection device is deployed. The guiding catheter has a balloon 31 around its tip, which is inflated to anchor the catheter with its tip at a distance 14 from the plaque's edge, typically approximately 0.5-1 cm in a large (approximately 6-8 mm) artery, but possibly as short as approximately 1-5 mm in a small or medium (approximately 2-6 mm) artery (FIG. 3A). Arterial diameter 15 at the plaque edge is measured angiographically and an edger tool is chosen having an open diameter at least approximately 10% larger than arterial diameter 15. Edger 40 is deployed through guiding catheter 30 (FIG. 3B) and expanded such that its fingers are slightly pressed against the arterial wall (FIG. 3C). This can be verified angiographically. Edger 40 is then rotated along its longitudinal axis and advanced towards lesion 12 (FIG. 3D). This separates the edge of plaque 12 from media 10, such that fingers 41 are in the SIS (FIG. 3E). The normal medial layer of the arterial wall has much higher axial flexibility (ultimate stretch greater than about 1.5) compared with the normal intimal layer, and these differences are exaggerated when comparing normal media to atherosclerotic intima in which both axial and circumferential flexibility are reduced (ultimate axial stretch of about 1.1-1.2). Calcified plaque elements are essentially rigid with an ultimate stretch of approximately 1.02 (See Holzapfel A G et al., "Anisotropic Mechanical Properties of Tissue Components in Human Atherosclerotic Plaques" *Journal of Biomechanical Engineering*, 2004, 126; 657-665). These differences in mechanical properties aid in the process of separation between the layers by the edger tool, which applies both circumferential and axial forces on all layers. The different response of each layer to these forces creates shear forces between the layers, which lead to their separation.

Figure 4A:
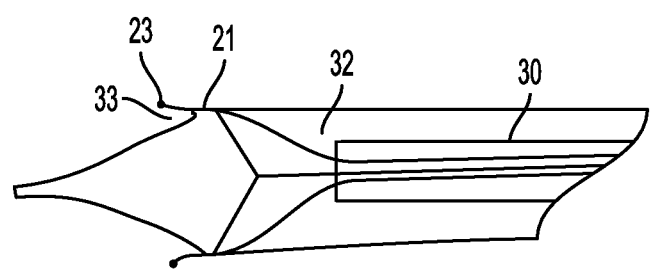
FIGS. 4A-B show the angiographic appearance of successful and failed edging.
Figure 4B:
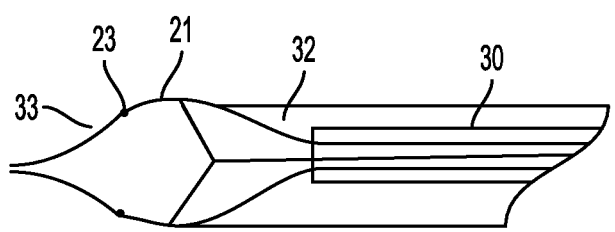

Optionally, verification of proper "edging" can be done angiographically, as seen in FIG. 4A-4B. FIG. 4A shows a schematic of an angiogram in case of successful edging. Edger 20 is shown through catheter 30 with radiopaque marker at the tip of finger 21. Filling defect 33 is seen between contrast material 32 and finger 21. FIG. 4B shows a schematic of an angiogram in case of unsuccessful edging. Edger 20 is shown through catheter 30 with radiopaque marker at the tip of finger 21. No filling defect 33 is seen between contrast material 32 and finger 21. As shown in FIG. 4A, the correctly positioned fingers are demonstrated external to the edge of the plaque, which is seen as a filling defect, whereas in FIG. 4B, the fingers are internal to the plaque edge, which means the edging was not successful.

Figure 5A:
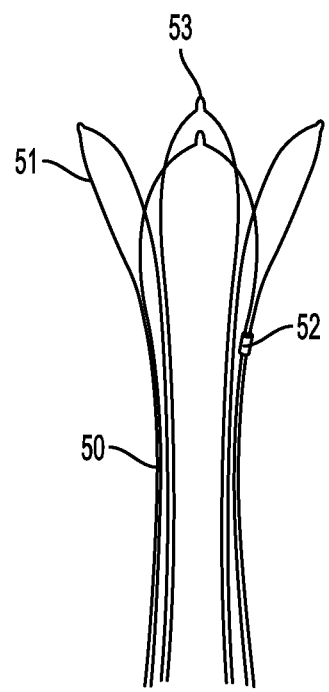
FIGS. 5A-C show embodiments of dissector tools in accordance with the principles of the invention
Figure 5B:
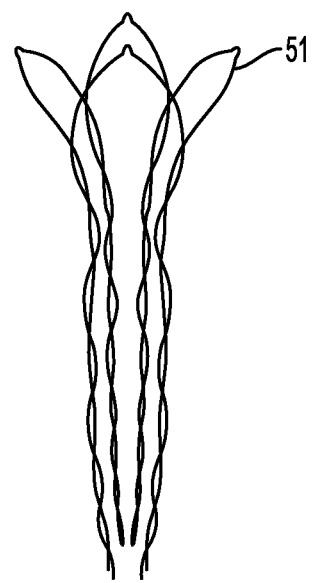
Figure 5C:
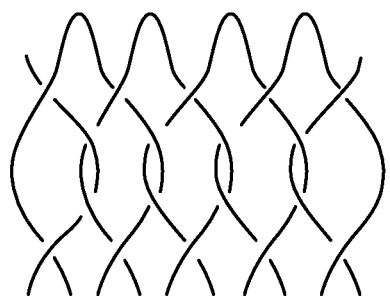

At this stage of the procedure, a dissector tool is introduced over the edger tool through the guiding catheter. An example of a dissector made of looped metal (such as nitinol) wires is shown in FIG. 5A-5C. More particularly, FIG. 5A shows dissector 50 made of wire loops 51, which may or may not be connected to each other by connector 52. The distal most part of each loop is at its centerline 53. FIG. 5B shows a similar dissector wherein each loop 51 is braided with the adjacent loop 51. FIG. 5C shows a possible more intricate pattern of braiding in which several loops are interlaced with each other.

The number of loops 51 in dissector 50 may vary between 2-8 but is typically 3-5. Loops may be completely separate as in 5A, or every two adjacent wires may be connected to each other by a connector 52. The braiding may be a simple one, involving only each two adjacent wires as in FIG. 5B, or more intricate including several loops as shown in FIG. 5C. Alternatively, such dissector may be formed of laser cut metal sheets or tube.

Figure 6A:
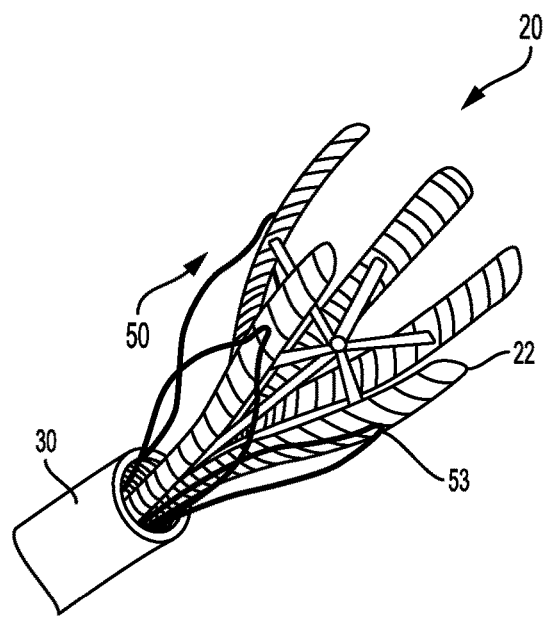
FIGS. 6A-B show use of one embodiment dissector tool in accordance with the principles of the invention.
Figure 6B:
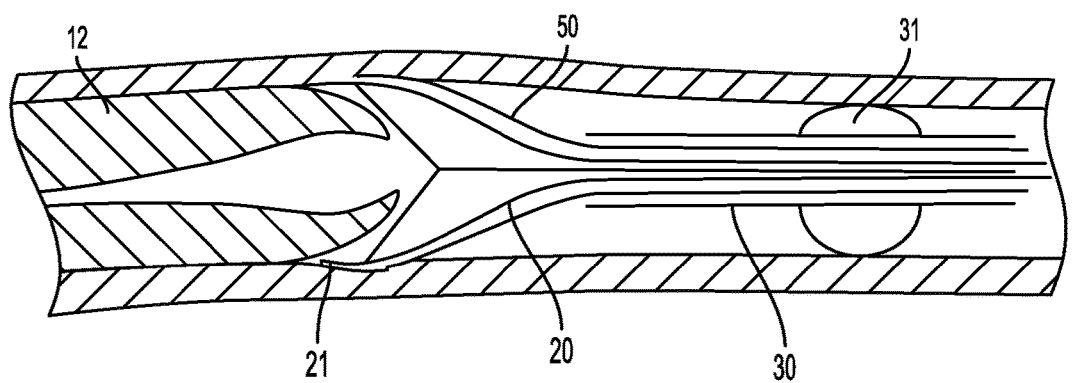

FIG. 6A-6B show use of dissector 50. More particularly, FIG. 6A is a three dimensional depiction of dissector 50, which is seen coming out of catheter 30, with its loop centerlines 53 over edger 20 finger centerlines 22. FIG. 6B shows a longitudinal section of an artery with plaque 12, and catheter 30 anchored by balloon 31. Dissector 50 is seen coming out of catheter 30 and being inserted into the SIS over edger fingers 21.

In use, as the dissector is pushed forward out of the guiding catheter (FIG. 6A), the user can rotate it to bring the centers of the loops 53 in line with the edger finger centerlines 21. Thus, the edger serves as a guide for the dissector into the SIS (FIG. 6B). Once the dissector loops pass the edger fingers, the edger can be retracted and removed. Optionally, the interior of guiding catheter 30 may be shaped with grooves that help align the edger and dissector tools.

The dissector is then advanced in the SIS under angiographic monitoring until it reaches the end of the lesion. Advancement of the dissector is achieved by a combination of forward push and rotation. The dissector loops will tend to expand as it is pushed forward, pressing against the flexible media and away from the more rigid plaque, which aids in the separation process.

Once dissector 50 passes lesion 12, dissector loop ends 53 might tear through intima 11 and enter the lumen without any action on behalf of the user. Such automatic re-entry may be enhanced by pre-shaping the dissector's nitinol loops with a curve towards the center of the lumen. However, this type of unintended re-entry carries a high chance of producing an intimal flap, which in turn might cause an arterial dissection, a dangerous complication of endarterectomy, which can lead to clogging of the artery, thrombosis, aneurysm or perforation. If an intimal flap is observed or suspected, it can be treated by placement of a stent over the transition area between the endarterctomized artery and untreated intima. In the current embodiment, in order to prevent the above, the dissector loops are shaped with an outward curve to reduce their tendency for re-entry. An intima cutting tool is provided as part of the dissector To enable smooth re-entry. Such tool 60 is shown in FIG. 7A-7E.

Figures 7A, 7B:
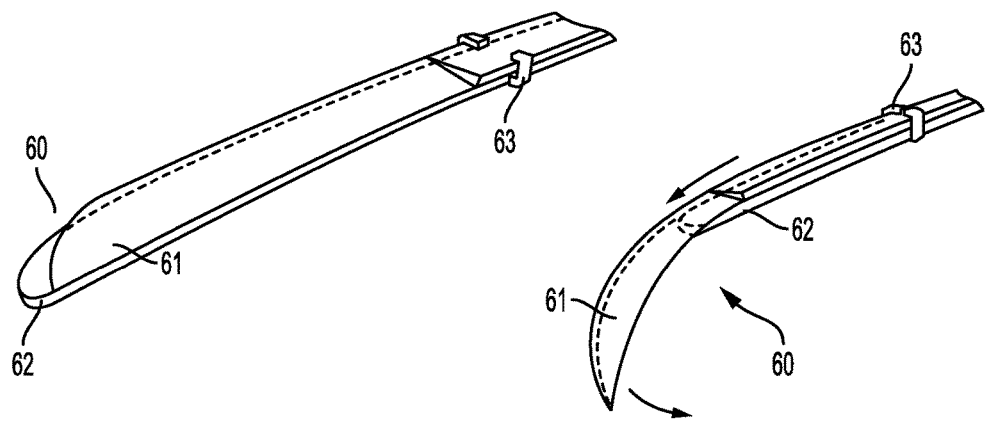
FIGS. 7A-E show embodiments of a distal intimal cutting tool in accordance with the principles of the invention.
Figures 7C, 7D:
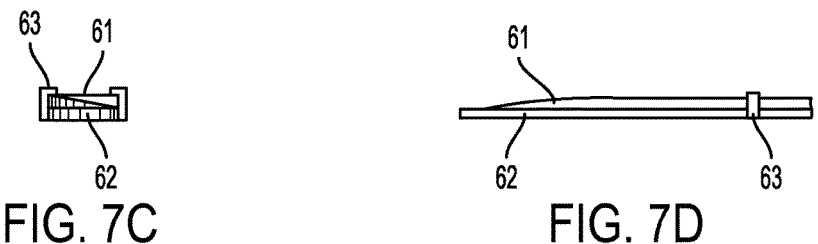
Figure 7E:
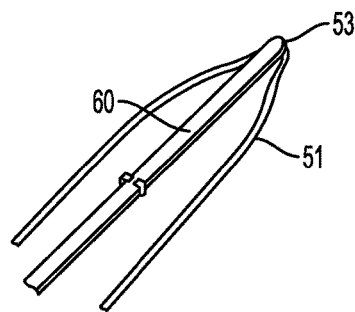
Figure 8A:
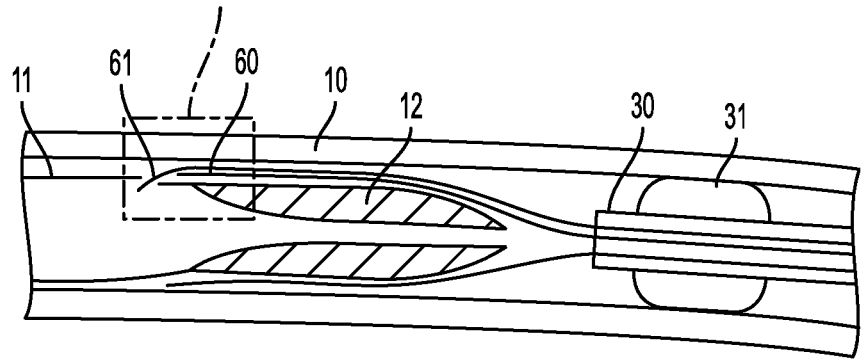
FIG. 8A shows use of one embodiment of a distal intimal cutting tool in accordance with the principles of the invention.
Figure 8B:
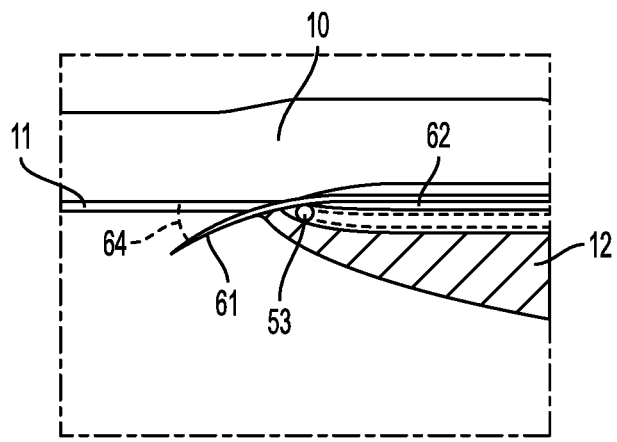
FIG. 8B shows a detail from FIG. 8A, which shows use of one embodiment of a distal intimal cutting tool in accordance with the principles of the invention.

More particularly, FIGS. 7A & 7B are three-dimensional depictions of intimal cutting tool 60 including blade 61 and guard 62, slideably held together by holder 63. FIG. 7A shows the closed position of cutting tool 60 whereas FIG. 7B shows the open position of cutting tool 60. FIG. 7C is an end view and FIG. 7D a side view of cutting tool 60. FIG. 7E shows typical assembly of cutting tool 60 over centerline 53 of loop 51 of dissector 50. FIGS. 8A and 8B show use of cutting tool 60 in a longitudinal section of an artery with media 10, plaque 12 separated by dissector 50, with cutting tool 60 over it, cutting through intima 11. A close-up view of the re-entry area is shown, with blade 61 sliding over guard 62 and loop centerline 53 of dissector 50, bending towards the lumen, and cutting through intima 11, creating an incision in intima 11 having an angle 64 with longitudinal axis of artery.

Intimal cutting tool 60 may be include two parallel metal strips, a blade 61, and a guard 62, held together by holder 63. Blade 61 has a sharp tip and side, whereas guard 62 has a rounded tip and blunt sides. Blade 61 is also pre-shaped with an arch, such that when slid forward over the guard, its sharp area is exposed and it arches to the direction of the guard. The cutting tool is typically attached to one of the dissector loop centerlines 53 (FIG. 7E). In use, when the dissector passes the lesion, the blade 61 is deployed (FIG. 8), penetrating through the intima in a sharp angle 64. The whole dissector is then rotated along its longitudinal axis such that the intima is cut all around the lumen, without leaving an intimal flap. The blade is retracted.

The entire intimal core is now completely separated from the arterial wall. The dissector is pulled backwards. This causes the loops to lengthen and the dissector's diameter to decrease, compressing the intimal core, and holding on to it. This enables removal of the complete core with the dissector.

The above was a general description of a preferred embodiment. Specific modifications of each stage and tool may be employed to improve performance of the invention. Following are some such modifications.

Figure 9A:
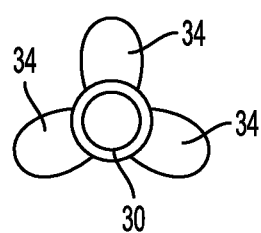
FIGS. 9A-B show cross-sectional views of two different embodiments of anchoring balloons for guiding catheter in accordance with the principles of the invention.
Figure 9B:
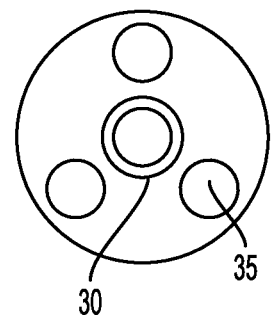

The anchoring balloon of the guiding catheter may be formed as several separate balloons (FIG. 9A), or having several conduits through it (FIG. 9B), to allow continuous blood flow across the treatment area during the procedure. This may be essential when the procedure is performed in areas that cannot tolerate cessation of blood flow, for example in case of treating a carotid artery when contralateral circulation is insufficient. Of course, in such a case, a distal protection device would be crucial. FIG. 9A shows catheter 30 surrounded by split balloons 34, and FIG. 9B shows a balloon having conduits 35 through it.

In a different embodiment of the edger tool, referring generally to FIGS. 10AA, 10BB and 10CC, the tool may include an elongated member from which end at least one "finger" (FIGS. 10AA & 10BB) but preferably three "fingers" (FIG. 10CC) or more "fingers" project retrogradely. Radial expansion of these fingers may be achieved by their being made of a shape memory alloy such as nitinol, or by other means or ways such as an inflatable balloon. Limitation of the radial expansion of the fingers for example by a slideable external sheath enables control over the degree of contact with the arterial wall and force applied to it. In one embodiment, the edger tool complete with the sheath is deployed through the guiding catheter which is anchored by the balloon. The sheath may function to only open and close the tool. The fingers are designed so that radial force applied by the fingers decrease going from the proximal to the distal end (relative to the plaque). In one embodiment, the fingers are parallel so that they do not cut the artery and so the fingers extend substantially in the direction of the dissection plane. The fingers are also so configured that they are more rigid towards the distal end and more flexible to the distal end. In another embodiment, the edges of the fingers may be sharp and the fingers configured to find the edge of the plaque without radially cutting the intima.

This "retrograde edger" tool is inserted through the guiding catheter placed proximal to the lesion. This tool is intended to be pulled back. It is passed beyond the lesion, deployed, then pulled back. The guiding catheter is used as a "base station". The guiding catheter is in place for passing any kind of tool and does not need to be part of the various devices. The edger is passed through the lesion until after its distal edge as seen on angiography. The sheath is withdrawn to allow radial expansion of fingers, which contact the arterial wall. The guiding catheter is away from the tool (see FIG. 11)

More particularly, FIGS. 10AA and 10BB show an "edger" tool generally shown by reference number 70. Edger tool 70 includes an elongated member 71 with a distal end 72 terminating in a distal tip 73. From elongated member 71 extends one finger 74 that extends retrogradely. For example, as shown, distal tip 73 may extend in one direction and a finger distal tip 78 may extend in another direction, preferably, retrogradely relative to a direction of distal tip 73. The relative positioning and direction of distal tips 73 and 78 may vary depending upon the positioning of finger 74 radially and/or relative to shaft 71. Finger 74 may move relatively freely and independently of shaft 71, in the embodiment shown, and may expand in a generally radial direction. In the illustrated embodiment, finger 74 is self-expanding. Radial expansion of finger 74 may be controlled by the intrinsic capabilities of the materials from which it is made and/or by external factors. For example, a slideable external sheath 75, enables control over the radial expansion of finger 74 and thereby the degree of contact with the arterial wall and force applied to it. FIGS. 10AA, 10BB and 10CC show the edger together with the sheath, which may be part of the edger device. Sheath 75 is a generally elongated hollow tube with a lumen passing through it. A distal end of guiding catheter 75 may include a side opening 76 and an open end 77. When distal end 72 of edger tool 70 is positioned in the distal end of sheath 75, edger tool 70 may be positioned as desired relative to sheath 75 to control positioning and radial expansion of finger 74. For example, in FIG. 10AA, finger 74 is positioned substantially away from side opening 76 and thereby is confined by sheath 75 so that finger 74 extends substantially alongside shaft 71. FIG. 10BB shows another position of edger tool 70 in sheath 75 where finger 74 is substantially disposed in side opening 76 as such finger 74 may be free to self-expand radially away from shaft 71. Typically, during delivery, sheath 75 is positioned relative to edger 70, such that open end 77 is proximate to finger distal tip 78, holding finger 74 essentially alongside shaft 71—"closed position." Edger 70 can then be passed through the lesion and deployed distal to it by sliding sheath 75 distally, bringing open end 77 over distal end 72—"open position". Sliding open end 77 back over finger 74 will gradually bring it adjacent to shaft 71, thus controlling its angle of opening.

As discussed above, edger tool may include one or more fingers. FIG. 10C shows an exemplary embodiment of an edger tool 79 with 3 fingers 74a, 74b, and 74c. This embodiment operates similarly to that described with respect to FIGS. 10AA and 10BB. With three fingers or more, edger tool 79 is kept centered in the arterial lumen by force of the fingers pressing against the arterial wall all around edger 79. This is in contrast to one finger, which may cause edger 70 to be pushed against the arterial wall opposite finger 75. Two fingers might cause the lumen's cross-sectional area to decrease as the artery is expanded radially at only two points on its circumference.

The fingers in accordance with the principles of the invention may include different configurations. For example, the fingers may have an overall shape and cross-section with specific profiles that enhance their ability to dissect the plaque from the arterial wall as shown in FIGS. 10A-10F and FIGS. 10G-10K. With references to FIGS. 10A-K, the fingers are flexible elongated fingers as shown. The fingers are configured to scrape and peel, but preferably are not sufficiently sharp to cut the plaque and/or intima. Furthermore, the distal tips of the fingers point towards the proximal end of the apparatus. Thus, these fingers are used for removing the plaque in a backwards motion. The shape, configuration and/or radius at the finger is not sharp as for cutting, rather it is blunt or sufficient to find the edge of the plaque through scraping without cutting the intima. The fingers are designed so that radial force applied by the fingers decrease going from the proximal to the distal end of the tip (relative to the plaque). Thus, in one embodiment, the fingers deliver more force on the proximal end of the finger and less force on the distal end. Alternatively, the force may change along the fingers in a non-linear manner, for example such that it is maximal at a certain distance along the fingers. In one embodiment, the tips of fingers are parallel to the shaft, thereby approximately parallel to how it engages the artery, so that the fingers do not cut the artery. The fingers preferably extend substantially along or in the direction of the dissection plane. The fingers are also so configured that they are more rigid towards the distal end and more flexible to the proximal end. Furthermore, the edges of the fingers may be relatively blunt, rounded, and/or curved so at to scrape along the plaque to find the edge and/or the separation of the plaque/layer. In one embodiment, the fingers are generally parallel to each other along their longitudinal sections. Preferably, the distal end results in a device that provides for a more gentle removal of the plaque. The embodiments shown are exemplary. As discussed above, the force differences can be achieved through structure (via e.g. use of structural features such as struts and guidewires or changing cross-section) or function (via e.g. use of a different materials). The device can be used in the methods described herein, including, being scraped along the plaque to find the edge and/or the natural separation of the plaque.

FIGS. 10A-B illustrate a configuration of fingers 80a, where each finger 80a is generally straight upon radial expansion. This shape will easily "dig" under plaques on the arterial wall, as its straight edge is pointed towards them. However, it is more prone to puncture the arterial wall than are shapes described in FIGS. 10C-F. FIG. 10A shows an end view of a distal end of an embodiment of an edger tool having three (3) fingers and FIG. 10B shows a side view of the edger tool in FIG. 10A. Fingers 80a are spaced radially equal distances apart on a main shaft as shown in FIG. 10A. Fingers 80a, when fully deployed, are at an acute angle relative to a longitudinal axis of the shaft. Referring now to FIGS. 10C and 10D, three fingers are positioned on the elongated shaft similar to fingers 74 in FIGS. 10A-10B, however, fingers 80b have a different shape, they are configured in a curved shape. Thus, the part applying the most force on the arterial wall is not the tip but the curvature of finger 80b. This reduces the risk of arterial injury. Referring now to FIGS. 10E-10F, three fingers 80c, are positioned on the elongated shaft similar to fingers 80a, 80b, in FIGS. 10A-10D, however, fingers 80c, are configured in a bent shape. This combines the benefits of both fingers 80a and 80b: the bend provides for a slightly sharper tool touching the arterial wall compared with the curved 80b, thus improving its edging capability, while at the same time preventing penetration of the tip into the arterial wall. As discussed above, one or more fingers may be used, and the placement and configuration of each finger may vary. Moreover, the placement and configuration of fingers may differ from each other on the same edger tool.

Figures 10G, 10H, 10I, 10J, 10K:
FIGS. 10G-K show various cross-sectional shapes of a finger of the fingered shaft (edger) in accordance with the principles of the invention.

FIGS. 10G-10K illustrate alternative embodiments for cross-sections of a hypothetical finger, embodiments of which are described herein. The cross-section is taken transversely across a distal end of a finger on an edger tool, with the direction of advancement to the left. The cross-section of the finger may vary along its length. FIGS. 10G, 10H, 10J are symmetrical. They differ in their profiles.

The edging action includes dissecting and wedging actions. "Dissecting" refers to the initial penetration between the layers, and "wedging" refers to their separation. The wedging action is mainly dependent upon the tool's wedge angle 82. Increasing this angle for a given length will increase the forces separating the plaque from the media. This will also increase the torque required to rotate the tool, therefore selection of specific tool wedge angle may be done by the physician during the procedure. FIG. 10G shows a cross-section of fingers having a small wedge angle, which will allow for low torque dissecting, but will be limited in the wedging action. FIG. 10H shows a cross-section of fingers having a larger wedge angle, which will require higher torque for the dissecting action, but will apply larger wedging forces. FIG. 10J depicts a finger cross-sectional shaping that is designed to reduce the required torque for the edging action. It does so by changing the wedge angle along the tool, so that a deeper penetration is achieved before the larger angled part of the finger induces the separating forces. FIGS. 10I and 10K, both having an asymmetrical cross-sectional shaping, are examples of possible design solutions that utilize finger shaping to exert forces on the fingers, directing them towards the separation plane.

The retrograde edger tool is rotated around its axis and simultaneously retracted so that the finger edges perform a spiral movement on the arterial wall. This movement gradually separates the plaque edge from the arterial wall (FIG. 11).

Figure 11:
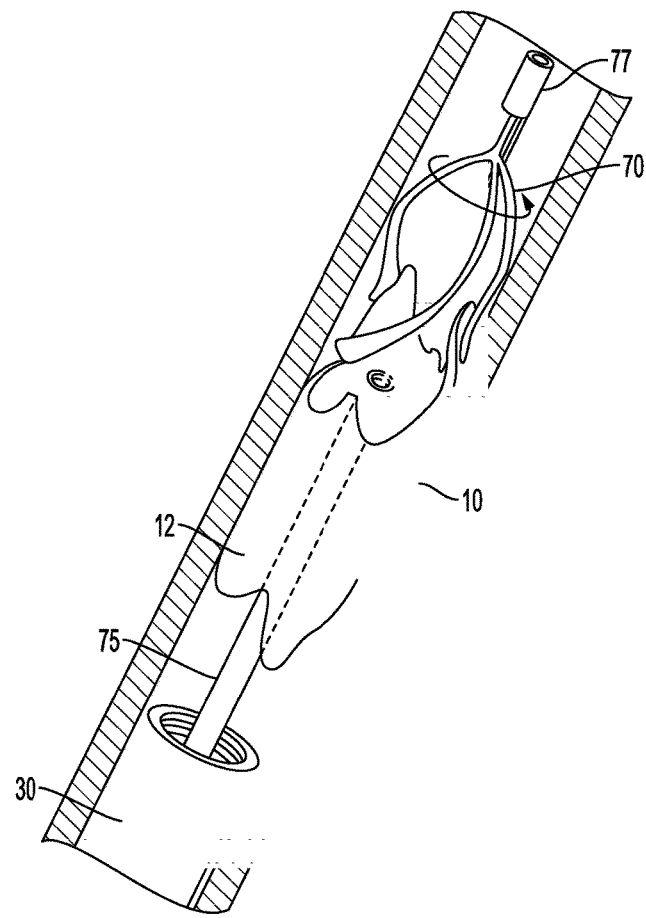
FIG. 11 shows use of a fingered shaft (edger) in accordance with the principles of the invention.

More particularly, FIG. 11 shows retrograde edger tool 70 in action. Artery with media 10 is seen in longitudinal section, plaque 12 is shown in 3D for demonstration purposes. Edger 70 has been deployed by pushing sheath 75 distally, after being passed through guiding catheter 30 and plaque 12. Edger 70 is in the fully open position, and is being rotated and pulled back thereby scraping, pealing and lifting the edge of the plaque. This is done, preferably, without cutting or damaging the artery.

Figure 12:
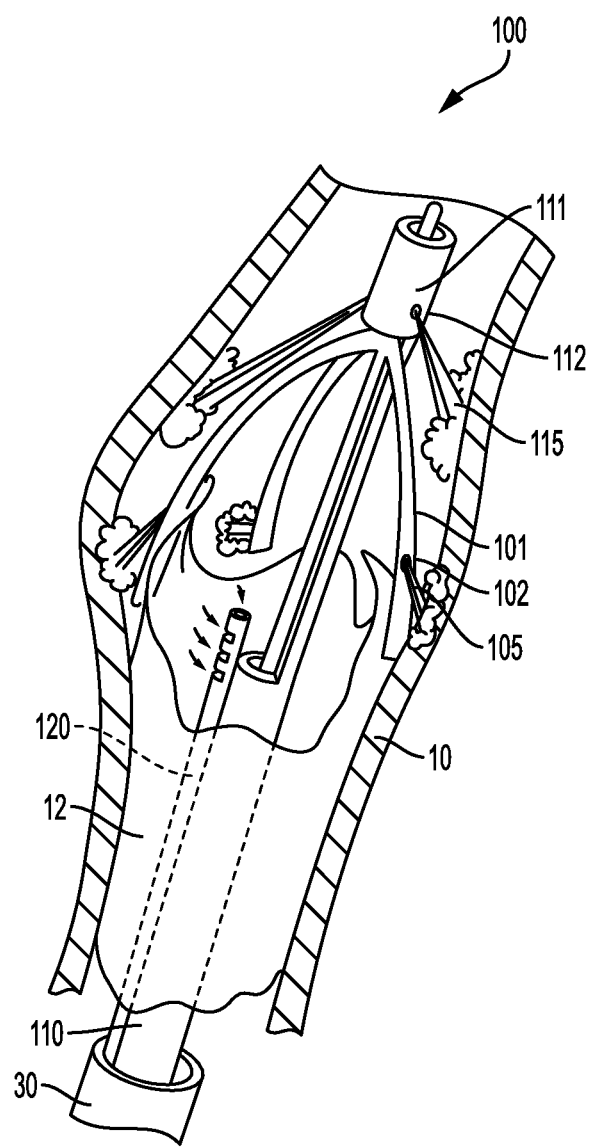
FIG. 12 shows use of a fingered shaft (edger) with saline jet in accordance with the principles of the invention.
Figure 13A:
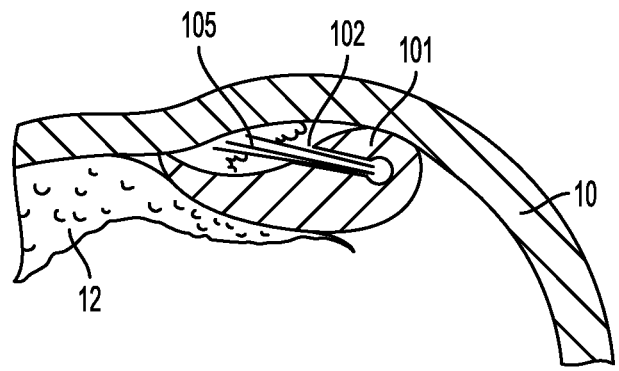
FIG. 13A-C show cross-sectional view of the finger and showing a saline jet exiting finger of the fingered shaft in accordance with the principles of the invention.
Figures 13B, 13C:
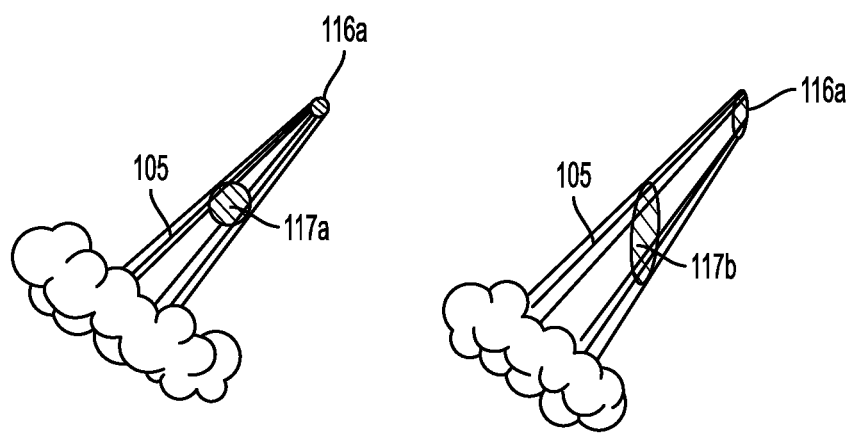
Figure 14:
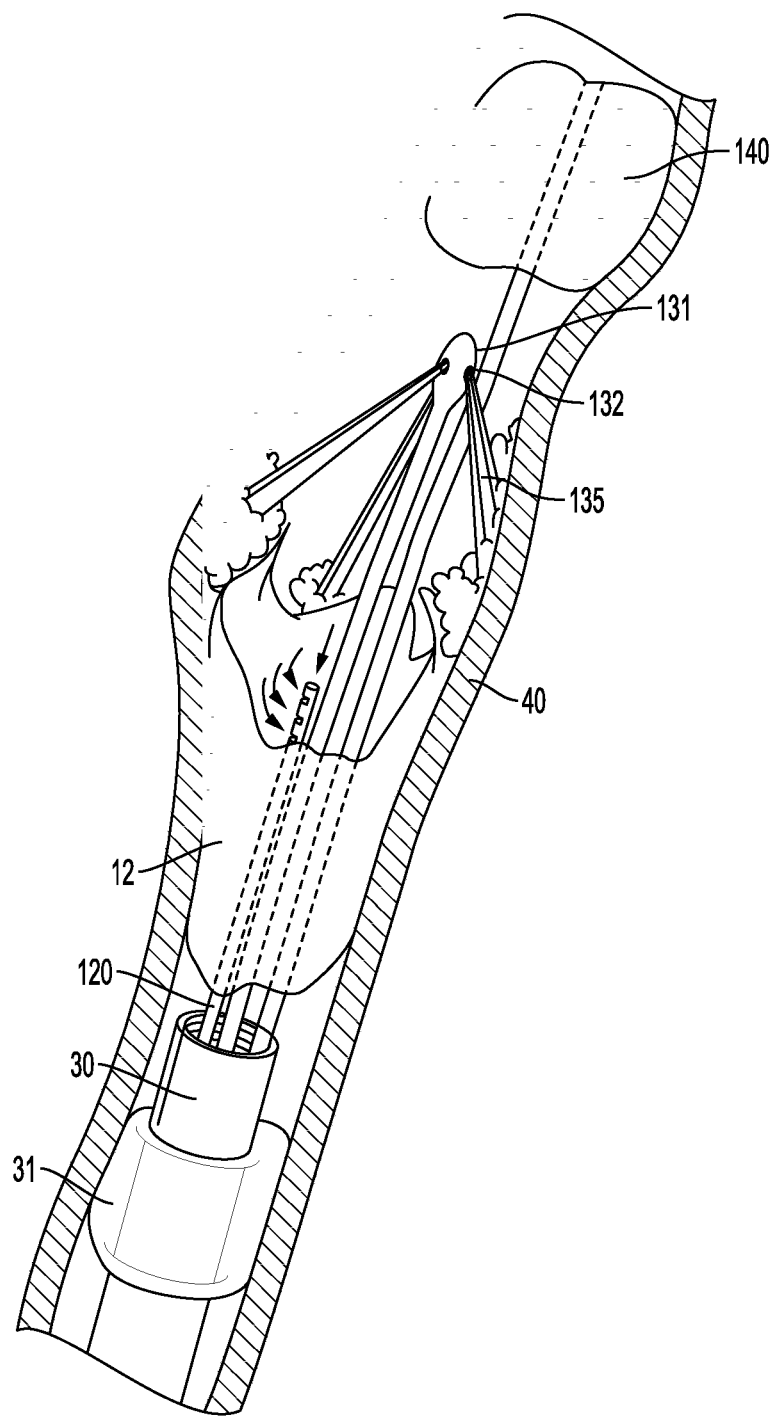
FIG. 14 shows use of edging and dissection tool employing saline jet and no fingers in accordance with the principles of the invention.

As an adjunct to the above, a jet of saline or other biocompatible fluid may be used to assist in the dissection, shown, for example, in FIGS. 12-14.

FIG. 12 shows guiding catheter 30 in artery with media 10 seen in longitudinal section, plaque 12 in three-dimensional. Jet edger tool 100 deployed with sheath 110 positioned such that fingers 101 are at fully open position. Open end 111 has nozzle 112 emitting jet 115. Fingers 101 have nozzles 102 emitting jet 105. Suction tube 120 removes excess fluids. Jets 115 and 105 aid in edging the plaque while edger 100 is rotated and pulled proximally.

Suction of excess fluid out of the blood vessel to prevent an undesirable increase in pressure may be performed through suction tube 120 as shown in FIG. 12. Suction may be used in combination with any of the embodiments described herein. Suction may be controlled either by keeping the net volume of injected fluid below a certain threshold, or by keeping the pressure in the vessel below a certain threshold.

Such a jet may be directed towards the arterial wall through the above-mentioned fingers as shown in FIG. 13A. The jet may be constant or intermittent, fixed or pulsatile. The jet may form a cross-sectional shape that is circular, elliptical or any other shape as shown for example in FIGS. 13A-C. FIG. 13A shows cross-section through artery and finger, depicting media 10 and plaque 12 being separated by finger 101, while nozzle 102 emits jet 105. FIG. 13B shows circular nozzle 116a emitting jet 105 having circular cross-section 117a. FIG. 13C shows elliptical nozzle 116b emitting jet 105 having elliptical cross-section 117b. A jet with an elliptical cross-section may be more effective in dissection than a jet with a circular cross-section when directed at the arterial wall with its longitudinal axis parallel to the arterial longitudinal axis.

Such a saline jet can be used instead of the fingers as shown in FIG. 14. FIG. 14 shows artery with media 10 seen in longitudinal section, plaque 12 in three dimensions. Guiding catheter 30 has balloon 31 inflated. Balloon 140 is placed and inflated distally. Jet edger tool 131 has nozzle 132 emitting jet 135. Suction tube 120 removes excess fluids. Jet 135 edges and dissects the plaque while edger 100 is rotated. In this embodiment, both edging and dissection may be performed by jet only, while the treated area is isolated between the two balloons. Alternatively, a similar jet edger tool may be used in anterograde fashion, when passage through the lesion is not possible, for example on a lower limb. Distal isolation may be achieved by external compression of the limb. Mixing contrast material with the jet fluid can enable angiographic visualization of the progression of subintimal dissection.

The tools described herein may be used under direct vision by endoscopy or other visualization method, as can optionally be done with all the edger and dissection tools described herein.

Figure 15:
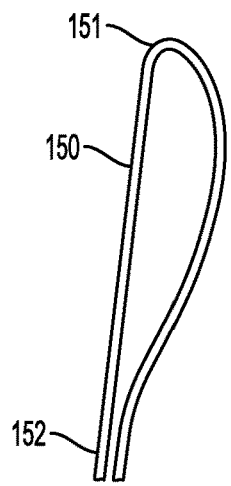
FIG. 15 shows an alternative embodiment of an edger tool finger in accordance with the principles of the invention.
Figure 16A:
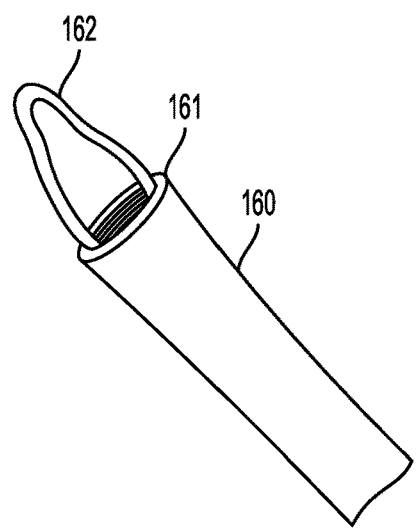
FIG. 16A-B show an embodiment of a combined edger and dissector tool in accordance with the principles of the invention.
Figure 16B:
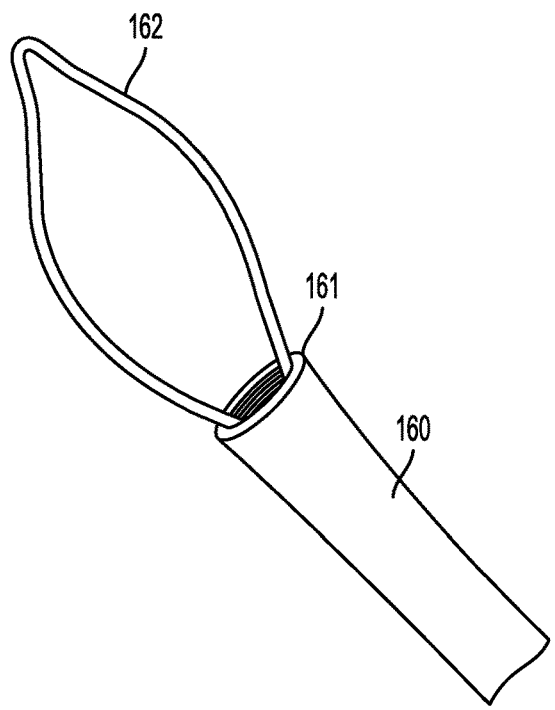

An alternative embodiment of the edger tool pertains to the structure of the fingers. As shown in FIG. 15, the fingers can be made of looped metal wires, or a laser cut metal tube or sheet. FIG. 15 shows wire 150 bent at point 151, with both ends returning to the base 152. Alternatively, the edger fingers can be made of metal tubes through which are passed metal wires. FIG. 16A shows such metal tube 160, compressed at its distal tip 161, and metal wire 162 extending therethrough. 16B is the same finger with wire loop slightly more distally extended. This structure can enable combining both edger and dissector into one tool, such that after edging is performed, the wire loops 162 can be extended into the SIS from the edges 161 of the fingers 160.

Figure 17:
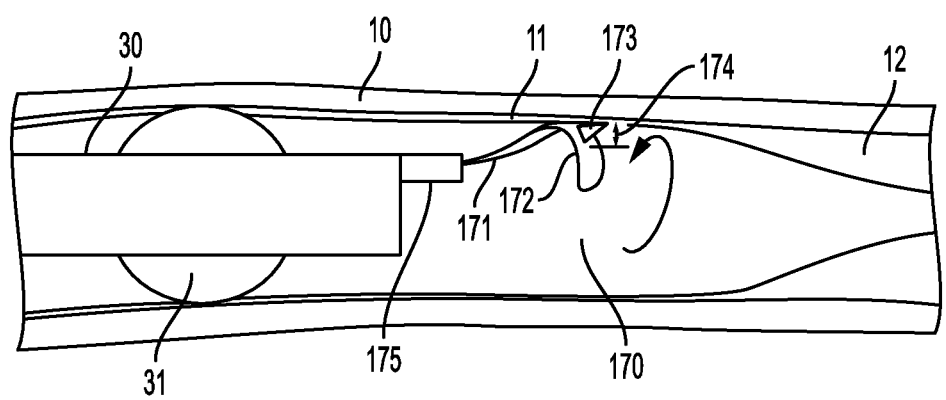
FIG. 17 shows an embodiment of a cutting tool in accordance with the principles of the invention.

An alternative approach to entering the SIS is based on an intentional cut of the intima, proximal to the lesion. This can be done using a specialized tool with a blade of predetermined depth. This is shown in FIG. 17: catheter 30 with balloon 31 in artery with media 10 and normal intima 11 proximal to lesion 12. Proximal intima cutting tool 170 includes a metal strip having elongated shaft 171, which curves into a radial part 172 oriented circumferentially from which a distally inclined blade 173 of height 174 protrudes radially. Sheath 175, which covers the tool before deployment, is retracted to enable its expansion and contact with intima 11. Rotation of proximal intimal cutter 170 several times cuts a thin incision through the intima. The tool 170 is covered by sheath 175 and removed. This can later be followed by deployment of radially expansive dissector tool, which when expanded radially and advanced distally, find its way into the incision, and enters the SIS or an adjacent dissection plane within the media.

Another aspect of the invention is a dissector tool. Dissection and advancement of the dissector may be aided by vibration that may be applied to the tool, and/or saline jet dissection as previously described.

An example of a tool intended for separating the rest of the plaque from the arterial wall is shown in FIGS. 18A and 18B. This embodiment includes a cylindrical bag, which is rolled up or folded into a ring. The ring is mounted on an elongated member. The bag has longitudinal inflatable strips in it that can be inflated through the external edge of the elongated member. The tool is placed in the artery via the guiding catheter. The ring is inserted between the plaque and media of the artery, preferably over the edger tool. Inflation of the longitudinal strips causes the bag to open and lengthen while dissecting between the plaque and media. This and additional similar embodiments are depicted in FIG. 18c in side view.

More particularly, in FIGS. 18A-B, dissection tool is shown generally at 180. FIG. 18A is a three-dimensional view of the device while FIG. 18B is a longitudinal section through the artery and device. FIG. 18A shows inflatable dissection tool 180 which has longitudinal inflatable strips 183 configured in a funnel shape when inflated. The ends of the strips face inwards. The inflatable dissection tool further includes longitudinal bag 181 which is surrounded by the longitudinal inflatable strips 183 and folded bag 182 which is towards the distal end of the tool 189. The folded bag 182 may be integral with longitudinal bag 181. FIG. 18B shows media 10, plaque 12, already slightly separated at edge by edger tool. With reference FIG. 18B, Inflatable dissection tool 180 is depicted with its longitudinal bag 181 in the lumen and the folded bag part 182 in the SIS. Once the longitudinal strips are inflated, the device unfolds while dissecting further between the layers.

FIGS. 18C-F show alternate embodiments of a distal end of dissection tools as described above with reference to FIGS. 18A-B. FIG. 18C shows dissection tool 180 described above. FIG. 18D shows another aspect of a dissection tool 180a. This device is identical to 180 except the direction of folds is inwards instead of outwards. Compared to 180a, tool 180 has the advantage of pushing the media outwards, whereas tool 180a pushes the intima inwards towards the plaque, which causes more resistance. FIG. 18E shows another aspect of a dissection tool 180b. This tool is folded as a harmonica fashion instead of being rolled. FIG. 18F shows another aspect of a dissection tool 180c. Both 180b and 180c encounter less resistance to unfolding than do 180 and 180a, however, the method of making the folds is simpler in the rolled up devices 180 and 180a. Importantly, devices 180 and 180a can be made of braided stents instead of a polymer bag. Instead of using inflation, they can be unfolded for example by pushing the folded ring forward at several points with wires extending proximally through the guiding catheter.

Figure 19A:
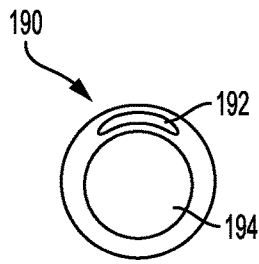
FIG. 19A-B show alternative embodiments of distal intimal cutting tools.
Figure 19B:
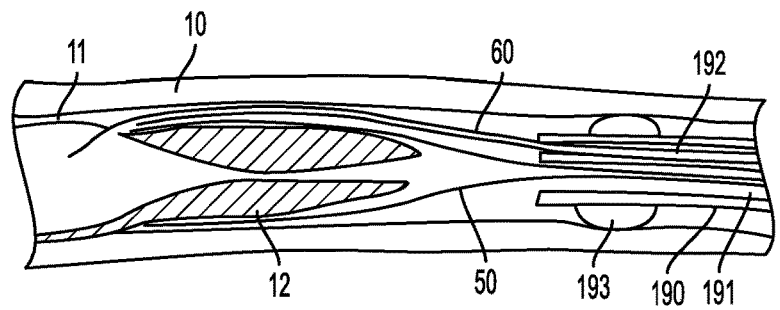

With regard to the distal intimal cutting tool, there are several additional embodiments. The distal intimal cutting tool 60 previously described may be inserted through a specialized groove located in the wall of the guiding catheter (FIG. 19A-B). 19A shows cross-section of multi-lumen guiding catheter 190 with catheter main lumen 191 and cutting tool groove 192. FIG. 19B shows a longitudinal section of the artery with cutting tool 60 extending from groove, inserted between media 10 and dissector tool 50, and cutting intima 11 at plaque edge. Alternatively, the cutting tool may be inserted through lumen 191 over or instead of dissector.

Figure 20A:
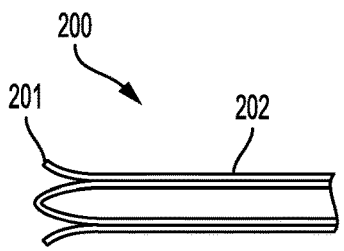
FIG. 20A-D show various embodiments of a distal tip of dissector tool loops.
Figure 20B:
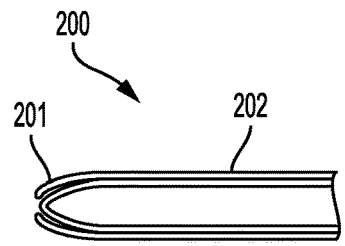
Figure 20C:
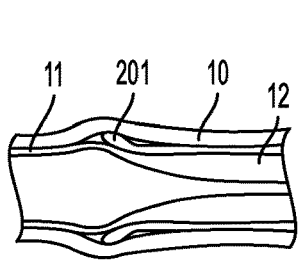
Figure 20D:
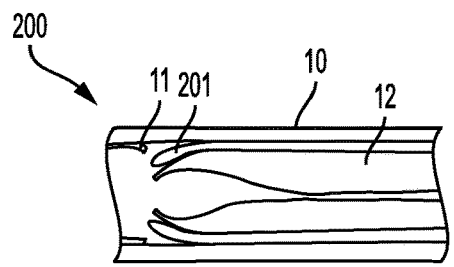

Another approach to cutting the intima at the edge of the lesion is based on the shape memory properties of the nitinol wires including dissector 200, shown in FIG. 20A-D. FIG. 20A shows dissector 200 having one or more dissector tip 201 at the distal end and loopwires 202, which is identical to dissector 50, apart from having been thermally treated to assume a thermally dependent conformation change. At normal body temperature, the dissector has a slight outward angulation of tip 201. FIG. 20B shows dissector after being heated/cooled—the angulation changes towards the interior of the lumen. FIGS. 20C-D show same in arterial longitudinal section. This change in angulation inwards can cause re-entry of the loops into the lumen. Alternatively, a needle may be extended from the edge of one of the loops, and after its entry into the lumen, a guide wire can be passed through it.

In some embodiments of the cutting tool, there are multiple tools on the dissector, each slideably attached to a loop's centerline. This allows for cutting around the whole intima with partial rotation of the dissector. After cutting and blade retraction, the cutting tools can be pushed forward such that they bend towards the center of the lumen and form a wall that assists in holding the plaque as it is pulled back and removed.

Medial Aspect:

This approach is based on threading a guidewire through the subintimal space from one end of the plaque to the other, then using a tool, which expands along this space, thus peeling the plaque from the arterial wall. This is intended to peel the plaque, which includes the intima, while leaving the media and adventitia intact. Sometimes, especially if the plaque involves the media, some medial layers might be peeled as well. However, this should not pose a major problem, as it often occurs during surgical endarterectomy, and does not cause any complications.

An embodiment of this approach is shown in FIGS. 21-23. A guidewire is introduced into the subintimal space and advanced along the lesion and beyond its far end, then back into the lumen. A separator device such as that shown in FIG. 23 (in its deployed state) is introduced over the wire (in its folded, non-deployed state). This tool includes a hollow cylinder with a longitudinal slit, folded onto an elongated member. When deployed, it assumes its cylindrical shape with an overlap of both ends over the slit.

This can be achieved for example by an inflatable balloon constructed of multiple longitudinal chambers having a trapezoid cross-section and connected to each other side by side. As the balloon is inflated, it dissects around the plaque, separating it from the arterial wall and encompassing the dissected plaque.

Figure 21A:
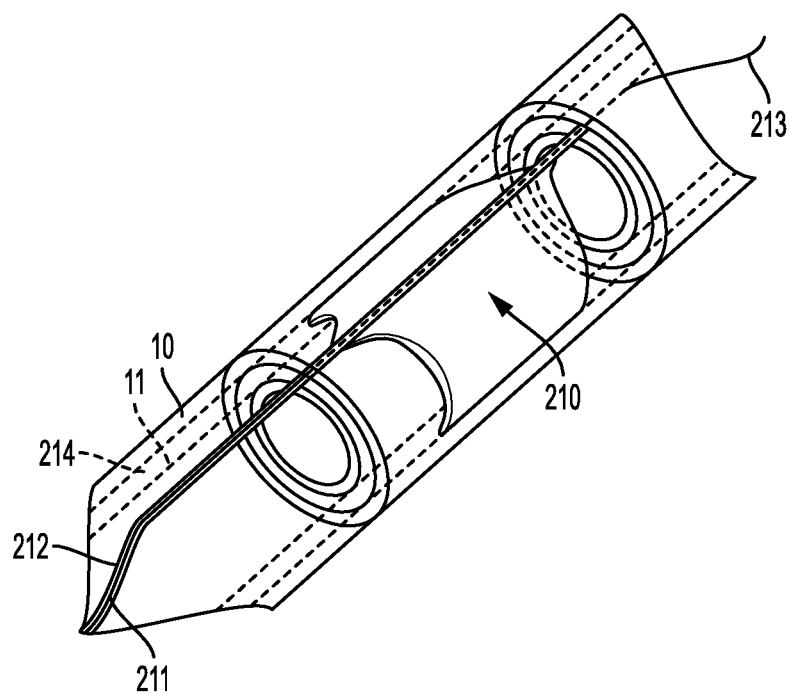
FIG. 21A-B show an embodiment of a medial plaque remover device.
Figure 21B:
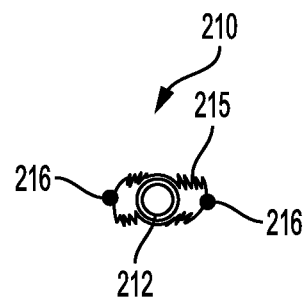

More particularly, with reference to FIG. 21A, a three-dimensional view of artery with deployed device 210 is depicted. Guidewire 211 inside device catheter 212 is seen intraluminally, then passes via intima 11 into subintimal space ("SIS") 214, and is again seen intraluminally 213 distal to lesion. FIG. 21B is a cross-section of device 210, folded balloon 215, catheter 212, and bilateral longitudinal radiopaque markers. The device may optionally have one or more longitudinal markers 216.

With reference to FIGS. 22A-F, the stages of this procedure are depicted. FIGS. 22A and 22B are longitudinal and transverse views of non-deployed device 210 passed over guidewire 211 in SIS, traversing lesion 12. FIGS. 22C and 22D are longitudinal and transverse views of device 210 partially deployed. FIGS. 22E and 22F are longitudinal and transverse views of device 210 at full deployment, encompassing lesion 12. FIG. 23 is a three-dimensional view of the deployed device 210 with catheter 212.

Prior to deployment, angiography can be used to ascertain the device is at the optimal orientation for deployment. Radiopaque markers 216 must be demonstrated parallel to each other at the medial border of the plaque. During deployment, the markers may be seen moving across the lumen to encompass the lesion.

After the device is fully deployed, a distal intimal cutting tool 60 can be used to free the connecting intima. Such tool 60 may either be integral with the dissector 210, or a separate tool used in combination with 210.

Figure 24:
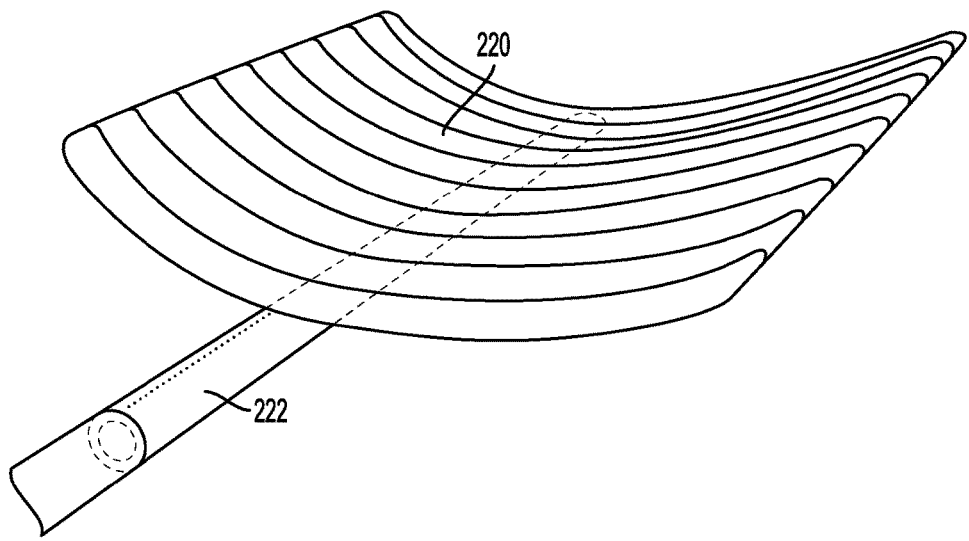
FIG. 24 shows a different embodiment of a medial plaque remover device in its inflated position.

Alternatively, a similar device 220 may be formed of transverse longitudinal strips, each having a slight curvature, such that when inflated the device assumes a flat shape, with only slight radius of curvature. This increases the tendency of the dissector to inflate within the SIS without encroaching on the arterial lumen. FIG. 24 is a 3D view of the flat device 220 with catheter 222.

Figure 25A:
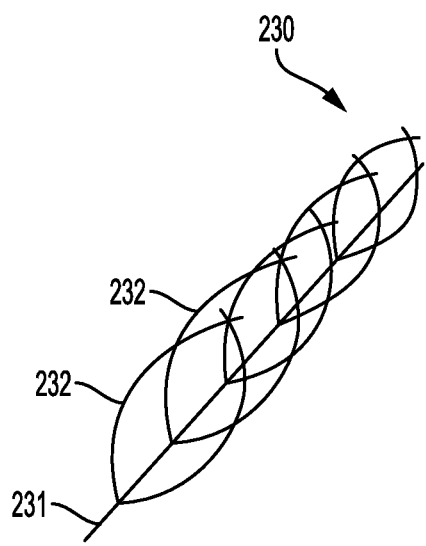
FIGS. 25A-C show an embodiment of a metal medial plaque remover device from different views.
Figure 25C:
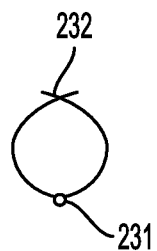
Figure 25B:
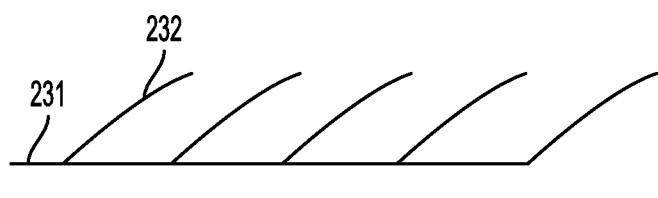

A different embodiment shown in FIGS. 25A-C is based on a nitinol device composed of multiple arched wires stemming off both sides of a central longitudinal spine. A sheath covers those "ribs" holding them flatly adjacent to the spine. When the sheath is removed, the ribs dissect around the plaque and form a cage encircling it.

More particularly, FIG. 25A shows device 230 at 3D. FIG. 25B shows a side view of device 230 shown in FIG. 25A. FIG. 25C shows and end view of device 230 in FIG. 25A. Ribs 232 extend laterally from spine 231

The above described devices 210, 220 and 230, which dissect and contain the plaque, may have a predetermined shape such that their distal end is closed. This allows for containment of the dissected plaque inside such structure, which prevents debris from embolizing. Alternatively, the distal end only or both ends may be closed for example by a wire traversing that end in a "purse-string," which wire can be tightened by pulling on such wire.

Inflating a balloon or deploying a nitinol web at the open end are additional ways for closing the aperture.

Removal of the freed plaque from the body can be achieved in several ways. If the volume of plaque is not very large, it may be possible to remove the plaque as is within the containment structure through the introducing sheath and outside of the artery. However, in some cases the plaque will be too large for such removal, and will need to be ground into small pieces.

Grinding the plaque can be done by a grinder mounted on a catheter, with a suction catheter as part of the same tool or used in conjunction with it. If the proximal end of the containment structure holding the plaque has been closed, it will need to be penetrated by such catheter to contact the plaque.

A useful addition to the above is a modification for preventing clogging of the grinder device.

In cases where the freed plaque was not contained in a bag or chamber, balloons should have been inflated on both sides of the work area to isolate it. Grinding and aspiration of the plaque can take place in this isolated area, followed by rinsing of the space with saline to ensure removal of all debris.

In some embodiments, after plaque removal, the treatment area is isolated between balloons and flushed with isotonic fluid in rapidly changing directions and pressure, in order to wash away any residual loosely adherent plaque, intima, or medial tissue. Alternatively or in addition, a fogarty catheter may be passed over the treated in a gentle manner. Other methods of ensuring removal of residuals include angiography, IVUS, or visual inspection.

Figure 28:
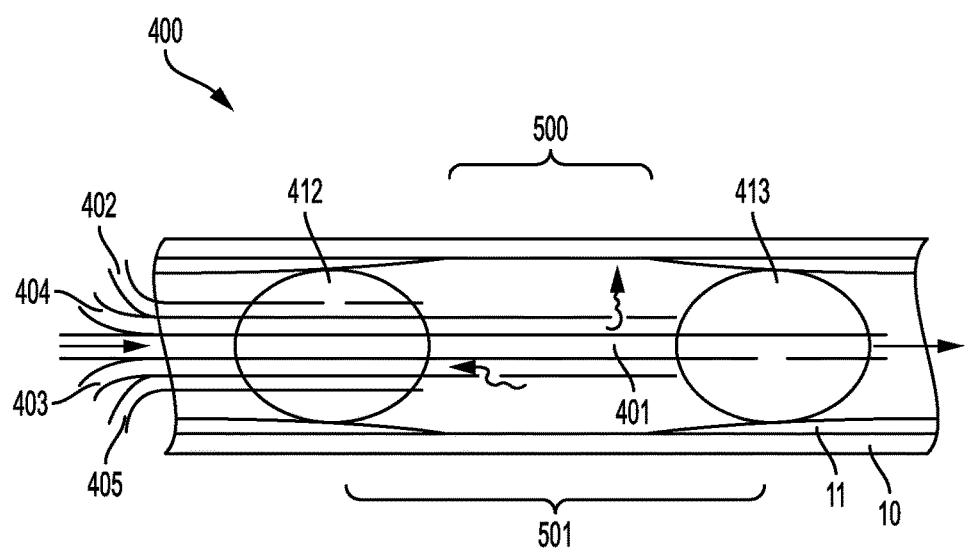
FIG. 28 shows an embodiment of a media treatment catheter device.

Following completion of the percutaneous atherectomy using the methods and devices described above, the next stage of treatment begins. FIG. 28 shows device 400 situated across area 500 where lesion was removed. Device 400 is a multilumen catheter intended for isolation of the treated area and delivery of medial layer therapy. Catheter 400 has lumen 401 for blood flow across isolated area 501. Lumen 402 inflates proximal balloon 412, lumen 403 inflates distal balloon 413. Lumen 404 serves for inflow of therapy and lumen 405 for outflow.

In use, proximal balloon 412 and distal balloon 413 are inflated. Blood passes freely through the blood flow lumen. Treatment may be delivered according to the specific protocol—e.g. perfusion with saline or blood, and instillation of the treating agent—usually endothelial progenitor cells. The treatment continues for the required duration. The area is flushed with saline and refilled with the patient's blood, the balloons are deflated, and catheter 400 removed.

Figure 26A:
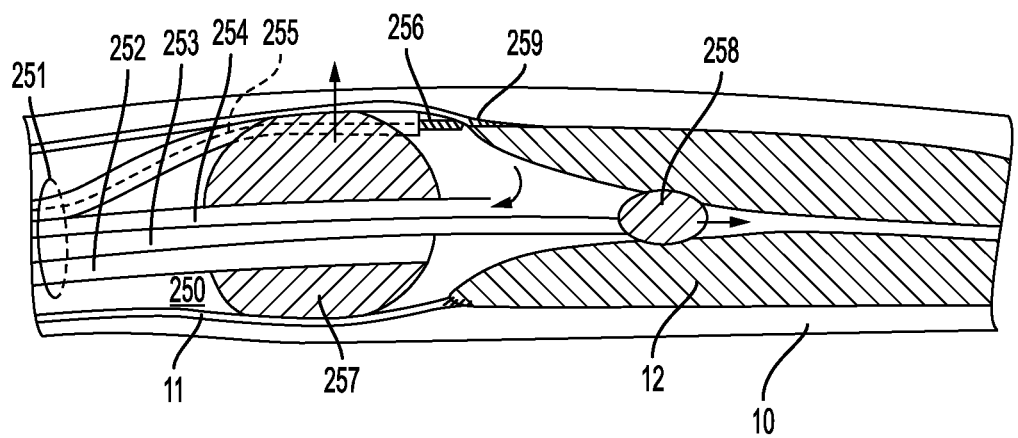
FIG. 26A-C show embodiments of subintimal wire insertion devices.
Figure 26B:
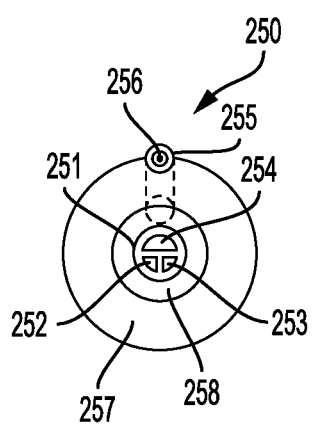

Another aspect of the current invention includes devices for insertion of guidewires into the SIS. Such a device intended for non-CTO lesions is shown in FIGS. 26A-B and includes a multilumen catheter, proximal and distal balloons, a suction lumen, and a catheter for passing a guidewire extending across the periphery of the proximal balloon. FIG. 26A is a longitudinal section through artery and device 250 showing device catheter 251, proximal balloon lumen 252, distal balloon lumen 253, suction lumen 254, guidewire catheter 255, guidewire 256, proximal balloon 257, distal balloon 258. FIG. 26B is a front view of same device. In use, device 250 is brought proximate to the plaque edge such that distal balloon 253 is within lesion. Proximal balloon 257 is inflated, followed by distal balloon inflation. Inflation of the balloons produces a force pushing the plaque distally and normal artery proximally, as well as an outward force on the arterial wall proximal to the lesion. These forces apply tension on transition zone 259 between "normal" intima 10 proximal to the lesion and plaque 12. The pushing force between the plaque and proximal artery may be increased by making distal balloon 253 moveable forward relative to guidewire catheter 255. The guidewire catheter is compressed against the arterial wall by the proximal balloon, and assumes an angle up to approximately 5 degrees outwards of the longitudinal arterial axis, leading the guidewire towards transition zone 259. Optionally, suction may be applied to the suction lumen, reducing the pressure in the area between the balloons and pulling the plaque away from the arterial wall towards the center of the lumen. The combination of increased tension in transition zone 259, exact direction of the guidewire towards transition zone 259, and pulling of plaque 12 away from arterial wall 10, facilitates entry of guidewire 256 through transition zone 259 into SIS.

Figure 26C:
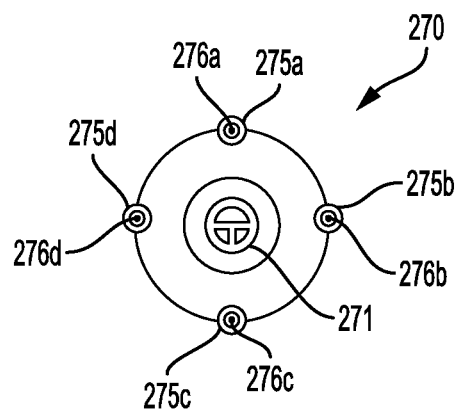

In another embodiment, a similar device 270 is provided for insertion of multiple guidewire around the lesion. FIG. 26C shows device 270 having device catheter 271 in front view with four guidewire catheters 275a-d leading four guidewires 276a-d into the SIS in the same manner described for device 250.

Figure 27A:
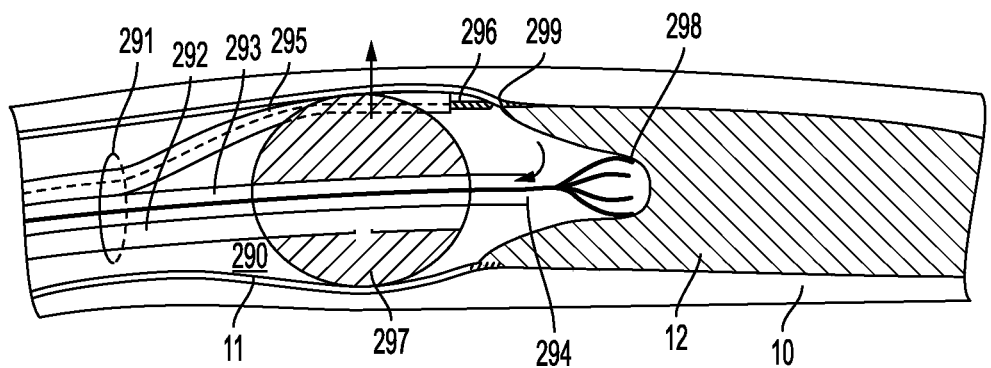
FIG. 27A-C show additional embodiments of subintimal wire insertion devices.
Figure 27B:
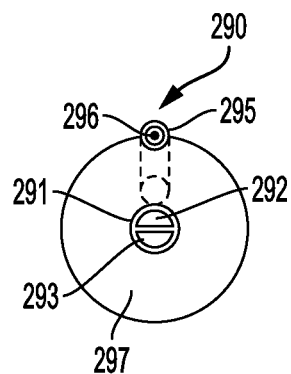
Figure 27C:
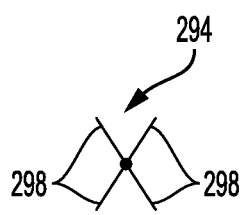

For CTO lesion or other lesions where a balloon cannot be inflated to within the lesion, a similar device is provided which uses an umbrella-like contraption instead of the distal balloon. FIG. 27A illustrates this device in an artery's longitudinal section. With reference to FIG. 27A, device catheter 291 is shown having proximal balloon lumen 292 and umbrella and suction lumen 293. The umbrella 294 is shown passing through the lumen of the device catheter 291. Guidewire catheter 295 containing guidewire 296 also passes the lumen of the device catheter 291. Umbrella 294 has umbrella distal end 298 FIG. 27B shows a front view of the catheter device and 27C a front view of the umbrella device. In use, device 290 is brought proximate to the plaque edge. Proximal balloon 297 is inflated, followed by deployment of umbrella 294. Inflation of the proximal balloon and pushing umbrella 294 forward produces a force pushing the plaque distally and normal artery proximally, as well as an outward force on the arterial wall proximal to the lesion. These forces apply tension on transition zone 299 between "normal" intima 10 proximal to the lesion and plaque 12. The guidewire catheter is compressed against the arterial wall by the proximal balloon, and assumes an angle up to approximately 5 degrees outwards of the longitudinal arterial axis, leading the guidewire towards transition zone 299. Optionally, suction may be applied to the suction lumen, reducing the pressure in the area between the proximal balloon 297 and plaque and pulling the plaque away from the arterial wall towards the center of the lumen. The combination of increased tension in transition zone 299, exact direction of the guidewire towards transition zone 299, and pulling of plaque 12 away from arterial wall 10, facilitates entry of guidewire 296 through transition zone 299 into SIS.

In yet another embodiment, a device based on the edger tool 20 can be used to deliver guidewires to the SIS. One or more guidewire catheters are attached to fingers 21 of edger, such that when edger fingers enter SIS or are proximate to it, pushing forward the guidewires will result in their entry to the SIS. Multiple such guidewires in the SIS can be used as a dissection means for short plaques or as a lead for insertion of a dissector too.

Figure 29:
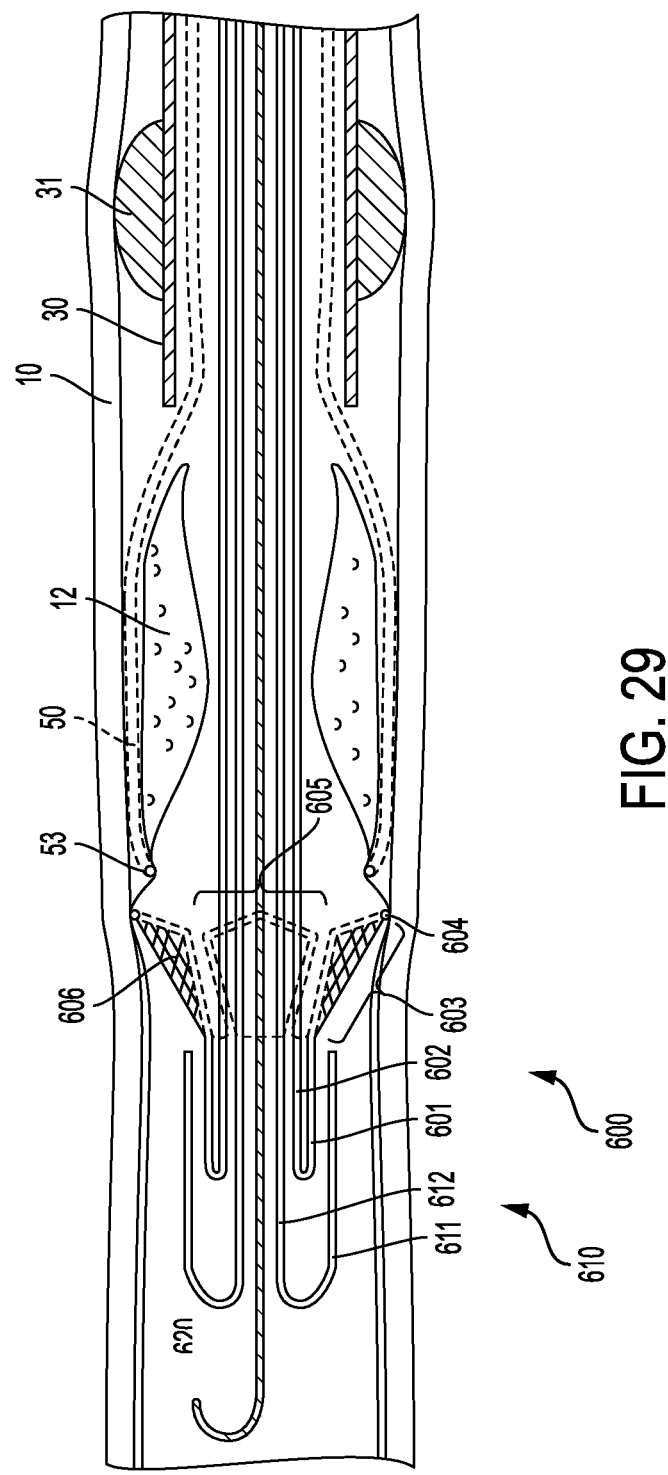
FIG. 29 shows an embodiment of a distal intima cutting tool.

Another embodiment of the invention is described in FIG. 29. This embodiment involves use of an anvil-like tool, which is placed distal to the lesion in order to assist with the distal intimal cutting stage. More particularly, FIG. 29 shows a longitudinal section of artery with media 10, plaque 12, guiding catheter 30 anchored by balloon 31. Anvil 600 is a cylindrical tool including body 601 continuous with elongated shaft 602, and several wings 603 each with distal tip 604 and distal edge 605. Wings 603 are formed such that when deployed, wings 603 flare outwards and distal edges 605 form an essentially continuous circumferential line around the inside of the lumen of the artery. Wings 605 may optionally be covered by web 606. Also provided is cap 610 including body 611 and elongated shaft 612. Body 611 is cylindrical and continuous with elongated shaft 612. Cap 610 can be pulled to cover Anvil 600, which folding wings 603 towards the elongated shaft 602. Elongated shaft 612 is threaded through elongated shaft 602, and both parts are passed through the guiding catheter 30, optionally over guidewire 620.

In use, anvil 600 is passed through guiding catheter 30 and inside lesion 12, and deployed distal to it by pushing cap 610 distally, such that anvil distal edges 605 press against the arterial wall and cause it to bulge outwards slightly. Web 606 of anvil 600 may then act as an emboli protection device. Edging or proximal intimal cutting is then performed in a manner similar to that described for previous embodiments, and dissection tool 50 is passed in guiding catheter 30 over elongated shaft 602 and through SIS until it reaches the distal plaque edge. At this point, pushing dissection tool 50 forward will cut intima between anvil distal edges 605 and loop centerlines 53. Cap 610 can then be pulled back to slightly close anvil 600 and dissector 50 to enable removal of all instruments together.

Using the anvil tool enables anchoring of the intima to the media during distal cutting, thus preventing or reducing the risk of creation of an intimal flap.

It is clear to anyone familiar with the art that the above described devices and methods can be used in any other organ in the body that has an elongated lumen such as the gastrointestinal tract, pulmonary system, urinary system etc.

Potential alternative applications of the above include but are not limited to biopsies, removal of tumors or pathological tissues.

Although the foregoing description is directed to the preferred embodiments of the invention, it is noted that other variations and modifications will be apparent to those skilled in the art, and may be made departing from the spirit or scope of the invention. Moreover, features described in connection with one embodiment of the invention may be used in conjunction with other embodiments, even if not explicitly stated above. The present invention may be embodied in other specific forms without departing from its spirit or essential characteristics. The described embodiments are to be considered in all respects only as illustrative and not restrictive.

What is claimed is:

1. A device for percutaneous removal of tissue, comprising:
   a hollow tube having a proximal and a distal end; and
   a tool configured to pass through the hollow tube, the tool having a distal end with two or more expandable loops, wherein an opening of a first of the two or more expandable loops is nonconcentric with an opening of a second of the two or more expandable loops,
   wherein the device is extendable along a longitudinal axis of the device, wherein the two or more expandable loops are configured to pass through a lumen of a vessel to access a subintimal space.

2. The device of claim 1, wherein the hollow tube is one of a sheath, a catheter, metal tube, and a finger.

3. The device of claim 1, wherein the tool is at least one of a dissector tool and an edger tool.

4. The device of claim 1, wherein the two or more expandable loops are wire loops.

5. The device of claim 1, wherein the two or more expandable loops are connected to each other by at least one connector.

6. The device of claim 1, wherein the two or more expandable loops are not connected to each other by a connector.

7. The device of claim 1, wherein the two or more expandable loops are connected to each other by a braid.

8. The device of claim 1, wherein the two or more expandable loops comprises anywhere from two through eight loops.

9. The device of claim 1, wherein the two or more expandable loops comprises four spatially equidistant loops.

10. The device of claim 1, wherein the two or more expandable loops forms a cross-section of the device that has a generally circular shape.

11. The device of claim 1, wherein each of the two or more loops has a center line and a leading distal tip, and the tissue comprises an inner layer of tissue and an outer layer of tissue, the leading distal tip being configured to remove the inner layer of tissue.

12. The device of claim 1, wherein each of the two or more expandable loops includes a proximal portion that is substantially straight along a longitudinal axis of the hollow tube and a distal portion comprising the loop that is radially expandable.

13. The device of claim 1, wherein the two or more loops are extendable along the longitudinal axis and along a radial axis of the device, wherein the two or more loops are configured to be expandable when extended.

14. The device of claim 1, wherein the tool is at least one of self-expandably, slideably and rotatably disposed in the hollow tube.

15. The device of claim 1, wherein the distal end of the two or more expandable loops is blunt.

16. The device of claim 1, wherein the two or more expandable loops are configured to remove a plaque from an arterial wall.

17. The device of claim 1, wherein the two or more loops expand when extended.

18. The device of claim 1, wherein the two or more expandable loops are adjustable in size.

19. The device of claim 1, wherein the two or more expandable loops are open loops, the open loops configured to expand when extended.

20. A device for percutaneous removal of tissue, comprising:
a hollow tube having a proximal and a distal end; and
a tool configured to pass through the hollow tube, the tool having a distal end with two or more expandable loops, wherein the two or more expandable loops are connected to each other by at least one connector,
wherein the device is extendable along a longitudinal axis of the device, and
wherein the two or more expandable loops are configured to pass through a lumen of a vessel to access a subintimal space.

21. A method of percutaneous removal of tissue, comprising:
(a) accessing the tissue with the device according to claim 1 having a hollow tube with a tool configured to pass through the hollow tube, and the tool having a distal end with two or more loops configured to remove the tissue; and
(b) utilizing the two or more loops of the tool to remove the tissue.

22. The method of claim 21, wherein the two or more expandable loops are connected to each other by at least one connector.

23. The method of claim 22, wherein each of the two or more loops has a center line and a leading distal tip, and the tissue comprises an inner layer of tissue and an outer layer of tissue, the leading distal tip being configured to remove the inner layer of tissue.

24. The method of claim 23, wherein the tissue to be removed is an atherosclerotic plaque.

25. The method of claim 24, after step (b) further comprising the step of utilizing a cutting tool that is configured to cut an intima connecting a distal part of the plaque to an arterial wall.

26. The method of claim 21, further comprising the step of utilizing the tool with a plurality of loops to remove plaque from an arterial wall around a circumference of the arterial wall.

27. The method of claim 21, wherein the two or more expandable loops comprises anywhere from two through eight loops.

28. The method of claim 21, wherein the accessing takes place in an artery, and wherein the utilizing the two or more loops of the tool to remove tissue removes tissue from an arterial wall.

29. The method of claim 21, wherein the utilizing the two or more loops includes extending the two or more loops along a longitudinal axis and along a radial axis of the device.

30. The method of claim 21, wherein the step of utilizing further comprises utilizing the two or more loops of the tool to remove an embolus from a blood vessel.

31. The method of claim 30, wherein the blood vessel is a pulmonary artery or a branch thereof.

* * * * *